ary Examiner—Melvyn I. Marquis

United States Patent [19]

Minagawa et al.

[11] 4,102,858
[45] Jul. 25, 1978

[54] 2,2,6,6-TETRAMETHYL-4-PIPERIDYL THIOCARBOXYLATES AND AMINOCARBOXYLATES AND SYNTHETIC RESIN COMPOSITIONS CONTAINING THE SAME

[75] Inventors: Motonobu Minagawa, Kosigaya; Naohiro Kubota; Toshihiro Shibata, both of Urawa, all of Japan

[73] Assignee: Argus Chemical Corporation, Brooklyn, N.Y.

[21] Appl. No.: 724,793

[22] Filed: Sep. 20, 1976

[51] Int. Cl.² .................. C07D 211/06; C08K 5/34
[52] U.S. Cl. ..................... 260/45.8 N; 260/293.63; 260/293.64; 260/293.81
[58] Field of Search ............. 260/45.8 N, 293.63, 260/293.64, 293.81

[56] References Cited

U.S. PATENT DOCUMENTS

| 3,939,168 | 2/1976 | Cook | 260/45.8 N |
|---|---|---|---|
| 3,939,170 | 2/1976 | Randell | 260/814 |

Primary Examiner—Melvyn I. Marquis
Assistant Examiner—H. H. Fletcher

[57] ABSTRACT

2,2,6,6-tetramethyl-4-piperidyl thiocarboxylates and aminocarboxylates are provided having the general formula:

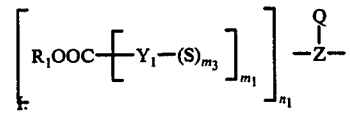

-continued

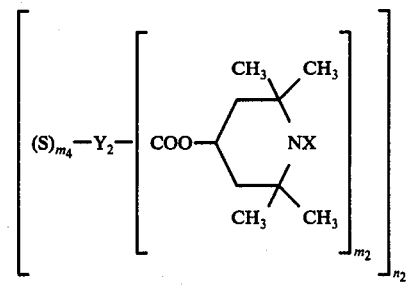

wherein:
$m_1$, $m_3$, and $m_4$ are numbers from 0 to 1;
$m_2$ is a number from 1 to 2;
$n_1$ is a number from 0 to 2;
$n_2$ is a number from 0 to 3;
$n_3$ is a number from 0 to 2;
$R_1$ is selected from the group consisting of alkyl, aralkyl, cycloalkyl and 2,2,6,6-tetramethyl-4-piperidyl;
$R_2$ is selected from the group consisting of alkyl, cycloalkyl, alkylaryl, aralkyl, and hydroxy-substituted such radicals;
$R_1$ and $R_2$ have from one to about twenty carbon atoms;
X is hydrogen or O;
$Y_1$ and $Y_2$ are bivalent linking radicals having from one to about 20 carbon atoms, and selected from the group consisting of alkylene and cycloalkylene; and amino-substituted such radicals;
Q is selected from the group consisting of $SR_2$ and

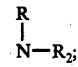

Z is an organic radical having a valence from 2 to 4 and from one to about twenty carbon atoms, and selected from the group consisting of alkylene, alkylidene, aralkylene, aralkylidene, alkarylene, alkarylidene, heterocycloalkylene, heterocycloalkylidene, cycloalkylene and cycloalkylidene; amino-substituted such radicals and 2,2,6,6-tetramethyl-4-piperidylidene;
there being from one to four sulfur-containing or nitrogen-containing such groups and at least one

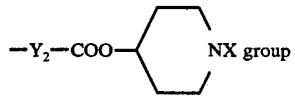

attached to the Z radical.

Synthetic resin compositions also are provided having their resistance to deterioration in the presence of ultraviolet light enhanced by at least one of these compounds.

58 Claims, No Drawings

2,2,6,6-TETRAMETHYL-4-PIPERIDYL THIOCARBOXYLATES AND AMINOCARBOXYLATES AND SYNTHETIC RESIN COMPOSITIONS CONTAINING THE SAME

Hindered 2,2,6,6-tetraalkyl-4-carboxylic acid ester piperidine compounds have been proposed by Murayama et al U.S. Pat. No. 3,640,928 patented Feb. 8, 1972 as light and heat stabilizers for synthetic polymers, such as polyolefins, polyvinyl chloride, polyvinylidene chloride, polyurethanes, and polyamides. These compounds have the general formula:

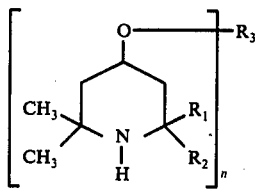

or a salt thereof.

In the above Formula:

$R_1$ and $R_2$ which may be the same or different, each are an alkyl group such as methyl, ethyl, isopropyl or dodecyl, or they form, together with the carbon atom to which they are attached, a saturated alicyclic group such as:

or a group of the formula

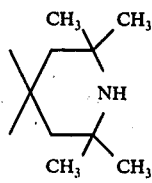

$n$ is an integer of 1 to 3 inclusive: and
$R_3$ is an acyl group.

These compounds have proved to be particularly acceptable because they do not impart a discoloration of their own to the synthetic polymer. The compounds generally employed previously have either been highly colored, such as the nickel compounds (which are normally green) and the 2-hydroxybenzophenones (which are varying shades and intensities of yellow). They also show very little tendency towards sublimation and exudation, and they have an excellent stabilizing action against both heat and light deterioration.

Consequently, the Murayama et al patent has been followed by a large number of patent and literature disclosures by Murayama et al and others of compounds including a 2,2,6,6-tetrasubstituted-4-piperidyl group attached to a base molecule of varying structures.

Murayama et al U.S. Pat. No. 3,898,303 patented Aug. 5, 1975 propose piperidino-spiro-hydantoin derivatives having the formula:

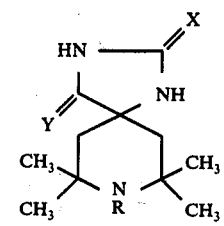

wherein
R represents an alkyl group, an alkenyl group, an alkenoyl group which may be substituted with an aryl group, a hydroxyalkyl group, an alkoxyalkyl group, an alkoxycarbonylalkyl group, an acyloxyalkyl group, a cyanoalkyl group or nitroso group, and X and Y individually represent oxygen atom or sulfur atom.

Murayama et al in U.S. Pat. No. 3,899,464 patented Aug. 12, 1975 disclose a variation of the piperidino spiro compounds having the formula:

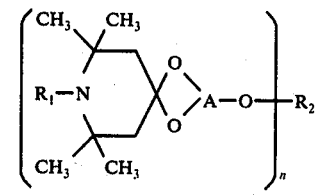

wherein
$R_1$ represents hydrogen atom, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, $n$ is an integer of 1 to 4;
when $n$ is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, N-substituted carbamoyl group, a N-substituted thiocarbamoyl group, a monovalent group from an oxoacid or group

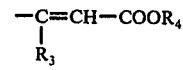

in which
$R_3$ represents hydrogen atom, a lower alkyl group or phenyl group and $R_4$ represents an alkyl group;
when $n$ is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid;
when $n$ is 3, $R_2$ represents an aromatic triacyl group or a trivalent group from an oxoacid; and
when $n$ is 4, $R_2$ represents an aromatic tetraacyl group, and A represents a group

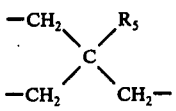

in which
R$_5$ represents hydrogen atom or a lower alkyl group or, when n is 1, R$_5$ may represent together with R$_2$ a group

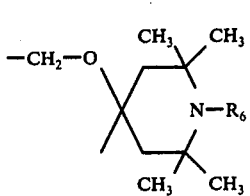

in which
R$_6$ represents the same group as defined in R$_1$ and may be the same or different from R$_1$, or a group

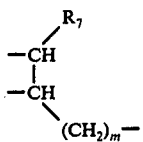

in which
m is 1 or 2 and R$_7$ represents hydrogen atom or, when n and m are 1, R$_7$ represents methylene group together with R$_2$.

Murayama et al U.S. Pat. No. 3,933,735 patented Jan. 20, 1976 propose 4-piperidone derivatives having a structure similar to the 4-piperidyl derivatives, but with a keto oxygen at the 4-position of the piperidine ring.

Murayama et al U.S. Pat. No. 3,941,744 patented Mar. 2, 1976, disclose another variation of the piperidino spiro derivatives having the formula:

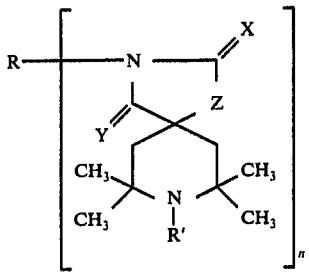

wherein
R' represents an alkyl group, a substituted alkyl group, an acyl group, an alkoxycarbonyl group, a substituted alkoxycarbonyl group, an amino group, a substituted amino group or nitroso group;
X represents oxygen atom or sulfur atom;
Y represents oxygen atom, sulfur atom or a group of the formula =N—R" in which R" is hydrogen atom, an alkyl group or a substituted alkyl group;
Z represents oxygen atom or a group of the formula >N—R'" is hydrogen atom, an alkyl group or a substituted alkyl group;
n is an integer of 1 through 4 inclusive; and
R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group, when n is 2, an alkylene group, an alkenylene group, an arylene group, a substituted arylene group, an aralkylene group, an alkylenediphenylene group, a bis-(acyloxyalkylene) group, an alkylene-bis-(oxycarbonylalkyl) group, a dialkylene ether group or a diphenylene ether group, when n is 3, an alkanetriyl group, a tris-(acyloxyalkylene) group, an alkane-tris-(oxycarbonylalkyl) group or a group of the group

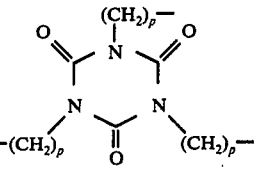

in which
p is an integer of 1 through 8 inclusive, and when n is 4, an alkane tetrayl group, a tetrakis-(acyloxyalkylene) group or an alkanetetrakis-(oxycarbonylalkyl) group.

Murayama et al U.S. Pat. No. 3,940,363 patented Feb. 24, 1976 disclose a further variation in which two 2,2,6,6-tetrasubstituted-4-piperidyl groups are linked together via the ring nitrogen atom to an R' alkylene linking group, which may be interrupted with an oxygen or sulfur atom, an alkenylene group, an alkynylene group, an aralkylene group, an aliphatic diacyl group, a group having the formula:

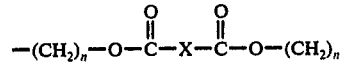

in which
n is an integer of 1 or 2 and X is an alkylene group, or o-, m- or p-phenylene group or the carbon atoms of CO groups may be directly joined in the absence of X or a group of the formula:

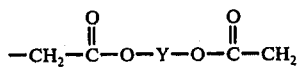

in which
Y is an alkylene group or o-, m- or p-phenylene group.

Ramey et al U.S. Pat. Nos. 3,899,491, patented Aug. 12, 1975 and 3,920,659, patented Nov. 18, 1975, disclose alkyl alkanoate derivatives of substituted piperazines and substituted piperazinodiones. The substituted piperazines of U.S. Pat. No. 3,899,491 have the formula:

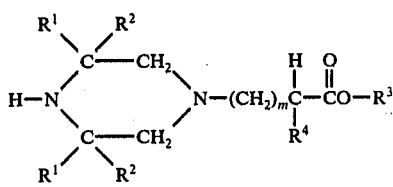

wherein $R^1$ and $R^2$ are methyl or together with the carbon to which they are bound form a mono-cyclic ring system having 5 or 6 carbon atoms;

$R^3$ is an alkyl group of from one to twenty atoms;

$R^4$ is hydrogen or methyl, and $m$ is 0 or 1.

The substituted piperazinodiones of U.S. Pat. No. 3,920,659 have the formula:

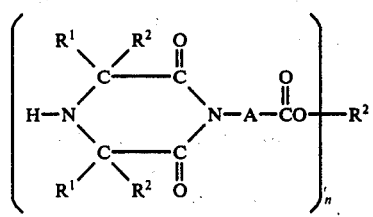

wherein $R^1$ and $R^2$ are independently of each other methyl or ethyl or together with the carbon to which they are bound form a cyclopentyl or cyclohexyl ring, which is unsubstituted or substituted with a methyl group;

$n$ is an integer of from 1 to 2;

when $n$ is 1, $R^3$ is an alkyl group of from 1 to 20 carbon atoms;

when $n$ is 2, $R^3$ is an alkylene group of from 2 to 8 carbon atoms; and

A is a straight or branched chain (lower) alkylene group containing from one to six carbon atoms with the limitation that the terminals of said alkylene group bear only hydrogen or one (lower) alkyl group.

Ramey et al U.S. Pat. No. 3,920,661 patented Nov. 18, 1975 disclose dicarboxylic acids and salts in which one carboxylic acid group is esterified with a 2,2,6,6-tetrasubstituted-4-hydroxy piperidine and having the formula:

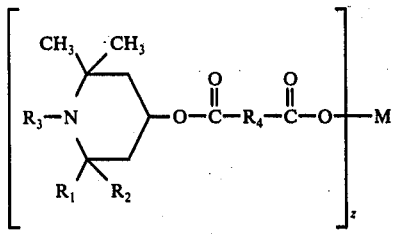

wherein $R_1$ and $R_2$ independently of each other are straight- or branched-chain alkyl having from one to six carbon atoms, or together with the carbon to which they are bound form a cyclopentyl or cyclohexyl ring, which is unsubstituted or substituted with a methyl group;

$R_3$ is hydrogen, alkyl having one to twelve carbon atoms, $\beta$-methoxyethyl, alkenyl having three or four carbon atoms, propargyl, benzyl or alkyl-substituted benzyl;

$R_4$ is straight or branched-chain alkylene having five to eight carbon atoms, or the group $(CH_2)_m Y(CH_2)_n$ wherein Y is oxygen or sulfur and $m$ and $n$ independently of each other are an integer from 1 to 3;

M is hydrogen or a metal selected from the group consisting of barium, nickel, manganese, calcium, zinc, iron, sodium, cobalt, tin, and dialkyl tin, and $z$ has a value of from 1 to 4, the value of $z$ being the same as the available valence of M.

Ramey et al U.S. Pat. No. 3,939,163 patented Feb. 17, 1976 disclose closely similar compounds in which $R_4$ is alkylene having from one to four carbon atoms.

Randell et al U.S. Pat. No. 3,939,170 patented Feb. 17, 1976 disclose dehydropyridinyl sulphides, sulphoxides and sulphones having the formula:

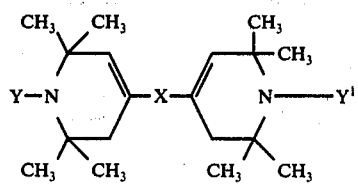

wherein

X is S, SO or $SO_2$ and Y and $Y^1$ are the same or different and each is H, OH, O- or a straight- or branched alkyl residue having from one to four carbon atoms, and salts thereof when Y and $Y^1$ are other than O-

Randell et al in published patent application No. B408,123 published April 13, 1976 disclose substituted piperidine-4-ols having the formula:

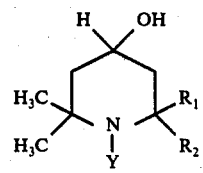

wherein $R_1$ and $R_2$ are the same or different and each is a straight- or branched alkyl residue having from 1 to 12 carbon atoms, or $R_1$ and $R_2$, together with the carbon atom to which they are attached, form a cycloalkyl residue having from 5 to 12 carbon atoms or the group:

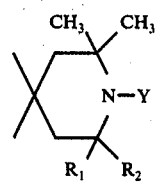

wherein $R_1$ and $R_2$ have their previous significance and Y is a straight- or branched alkyl residue having from 1 to 20 carbon atoms, an alkenyl or alkynyl residue having from 3 to 20 carbon atoms, an aralkyl residue having from seven to twelve carbon atoms or the group $-CH_2X$ wherein X is the group

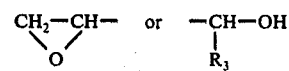

wherein $R_3$ is hydrogen, a methyl or phenyl residue, the group

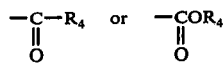

wherein
$R_4$ is an alkyl residue having from 1 to 20 carbon atoms.

Cook U.S. Pat. No. 3,929,804 patented Dec. 30, 1975 discloses 4-piperidine acetamide compounds having the formula:

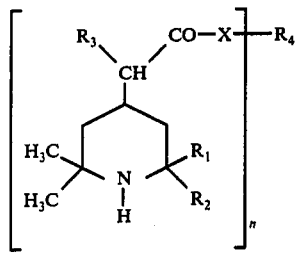

wherein
$R_1$ and $R_2$ are the same or different and each is a straight- or branched alkyl residue having from 1 to 12 carbon atoms, or $R_1$ and $R_2$, together with the carbon atom to which they are attached form a cycloalkyl group having from 5 to 12 carbon atoms;

$R_3$ is hydrogen, a straight- or branched alkyl residue having from 1 to 4 carbon atoms, an aralkyl residue having from seven to nine carbon atoms or a cycloalkyl group having from 5 or 6 carbon atoms;

$R_4$ is a metal ion or a hydrocarbyl residue having from two to twenty carbon atoms and being either unsubstituted or substituted by halogen or interrupted by one or more oxygen or sulphur atoms;

X is —O—, —S—, or >$NR_5$, wherein $R_5$ has the same significance as $R_3$; and n is 2, 3 or 4; as well as salts of the amine function of the compounds of formula I.

Cook U.S. Pat. No. 3,939,168 patented Feb. 17, 1976 discloses closely similar compounds having a Y substituent on the piperidyl nitrogen atom, Y being alkyl, alkenyl, aralkyl or a group

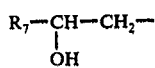

wherein:
$R_7$ is hydrogen, alkyl or phenyl.

In accordance with the invention, 2,2,6,6-tetramethyl-4-piperidyl thiocarboxylates are provided having the formla:

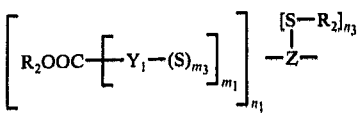

I.

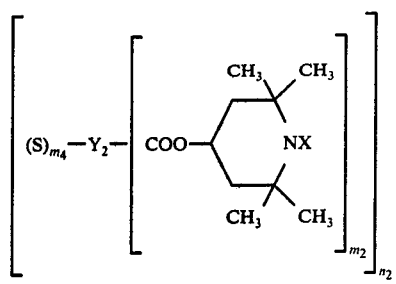

wherein:
$m_1$, $m_3$, and $m_4$ are numbers from 0 to 1;
$m_2$ is a number from 1 to 2;
$n_1$ is a number from 0 to 2;
$n_2$ is a number from 0 to 3;
$n_3$ is a number from 0 to 2;
$R_1$ is selected from the group consisting of alkyl, aralkyl, cycloalkyl and 2,2,6,6-tetramethyl-4-piperidyl;
$R_2$ is selected from the group consisting of alkyl; cycloalkyl; alkylaryl; aralkyl; and hydroxy-substituted such radicals;
$R_1$ and $R_2$ have from one to about twenty carbon atoms;
X is hydrogen or O;
$Y_1$ and $Y_2$ are bivalent linking radicals having from 1 to about 20 carbon atoms, and selected from the group consisting of alkylene and cycloalkylene; and amino-substituted such radicals;
Z is an organic radical having a valence from 2 to 4 and from one to about twenty carbon atoms, and selected from the group consisting of alkylene, alkylidene, aralkylene, aralkylidene, alkarylene, alkarylidene, heterocycloalkylene, heterocycloalkylidene, cycloalkylene and cycloalkylidene; amino-substituted such radicals and 2,2,6,6-tetramethyl-4-piperidylidene;
there being from one to four sulfur-containing such groups and at least one

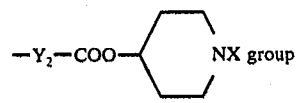

attached to the Z radical.

Synthetic resin compositions also are provided having their resistance to deterioration in the presence of ultraviolet light enhanced by at least one of these compounds.

Also provided in accordance with the invention are 2,2,6,6-tetramethyl-4-piperidyl aminocarboxylates having the formula:

II.

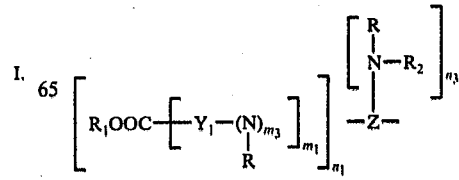

-continued

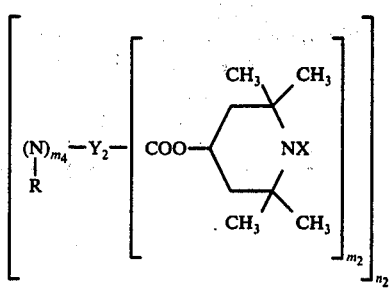

wherein:
$m_1$, $m_3$ and $m_4$ are numbers from 0 to 1;
$m_2$ is a number from 1 to 2;
$n_1$ is a number from 0 to 2;
$n_2$ is a number from 0 to 3;
$n_3$ is a number from 0 to 2;
R is selected from the group consisting of hydrogen, alkyl, hydroxyalkyl, aralkyl, cycloalkyl, alkaryl, 2,2,6,6-tetramethyl-4-piperidyl, $R_1OOCY_2$, phenyl, hydroxy phenyl and

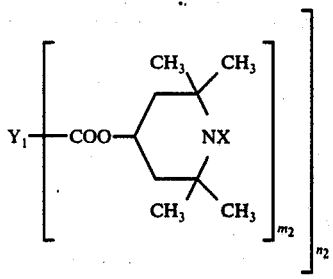

$R_1$ is selected from the group consisting of hydrogen, alkyl, aralkyl, cycloalkyl and 2,2,6,6-tetramethyl-4-piperidyl;
$R_2$ is selected from the group consisting of hydrogen, alkyl, cycloalkyl, aryl, alkaryl, aralkyl, and hydroxy-substituted such radicals,
R (when other than hydrogen), $R_1$ and $R_2$ have from 1 to about 20 carbon atoms;
X is hydrogen or O;
$Y_1$ and $Y_2$ are bivalent linking radicals having from one to about twenty carbon atoms, and selected from the group consisting of alkylene and cycloalkylene; and
Z is an organic radical having a valence from 2 to 4 and having from 1 to about 20 carbon atoms, and selected from the group consisting of alkylene, alkylidene, arylene, aralkylene, aralkylidene, alkarylene, alkarylidene, heterocycloalkylene, heterocycloalkylidene, cycloalkylene and cycloalkylidene; there being from one to four nitrogen-containing such groups, and at least one

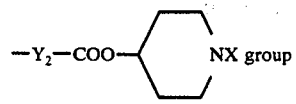

attached to the Z radical.

A preferred class of 2,2,6,6-tetramethyl-4-piperidyl aminocarboxylates are defined by the formula:

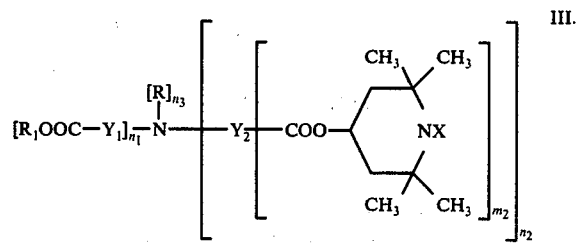

where R, $R_1$, $Y_1$, $Y_2$, X, $m_2$, $n_1$, $n_2$ and $n_3$ are as above, in Formula II.

$Y_1$ and $Y_2$ preferably are —$CH_2$, —$CH_2CH_2$—, >$CHCH_2$— or >$CHCH_2CH_2$—, $n_2$ is two or three, $n_1$ is zero or one, and $n_3$ is zero, one or two, and when $n_3$ is one or two, R is hydrogen.

Another preferred class of these aminocarboxylates are defined by the formula:

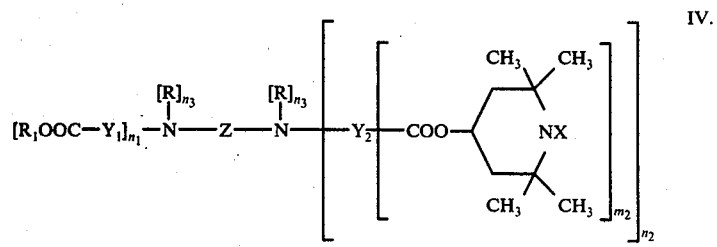

where R, $R_1$, $Y_1$, $Y_2$, X, $m_2$, $n_1$, $n_2$ and $n_3$ and Z are as above, in Formula II.

Z is preferably alkylene, phenylene, or alkylenecycloalkylene.

Synthetic resin compositions also are provided having their resistance to deterioration in the presence of ultraviolet light enhanced by at least one of these compounds.

The thiocarboxylate compounds are readily prepared from the mercaptocarboxylates of 2,2,6,6-tetramethyl-piperidine-4-ol. The corresponding mercaptocarboxylic acid is reacted with 2,2,6,6-tetramethyl-piperidine-4-ol to form the corresponding mercaptocarboxylate ester, and this compound is then attached to the corresponding —Z— radical by reaction with the free mercapto group of the mercaptocarboxylate.

The following procedure is illustrative:

EXAMPLE I 5.5 g of benzaldehyde was added slowly to a solution of 100 ml of benzene and 23 g of the thioglycolic acid ester of 2,2,6,6-tetramethyl-piperidine-4-ol below 20° C. The mixture was stirred for 1 hour below 25° C, and an additional 2 hours at 60° C.

The solvent was then distilled off, and the resulting residue of sticky material was dissolved in n-hexane, and stored for eight days under refrigeration. White crystals were obtained, having a molecular weight of 552, corresponding to the calculated molecular weight of 551 for the compound:

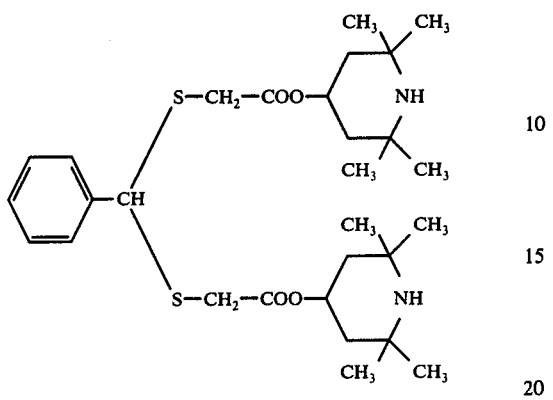

EXAMPLE II

A mixture was prepared containing 20 g of the maleic acid diester of 2,2,6,6-tetramethyl-piperidine-4-ol, 29 g of lauryl thioglycolate, 20 ml of tertiary butanol, and 2 ml of a 40% methanol solution of trimethylbenzyl quaternary ammonium hydroxide. The mixture was stirred at from 30° to 35° C for 2 hours, and then at 60° C for an additional 4 hours.

The butanol and methanol were distilled off, and the resulting colorless viscous liquid was dissolved in a small amount of petroleum ether and stored for 2 days at 5° C. A white powder was obtained. The molecular weight was found to be 655, corresponding to the molecular weight calculated for the compound:

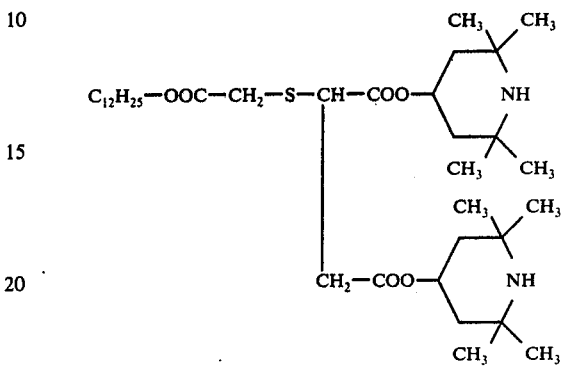

Using the above reaction procedures, the following additional compounds were prepared:

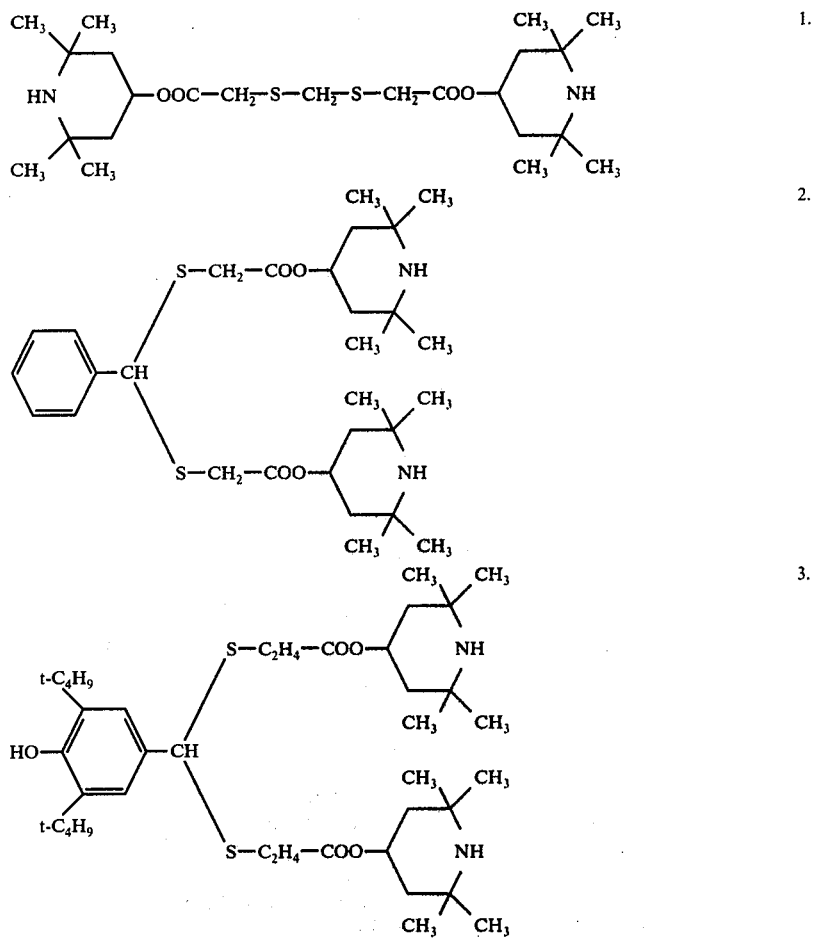

-continued
4.
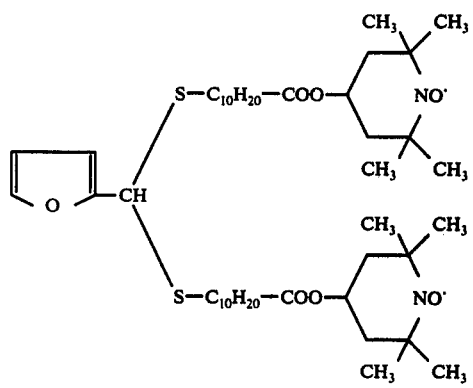
5.
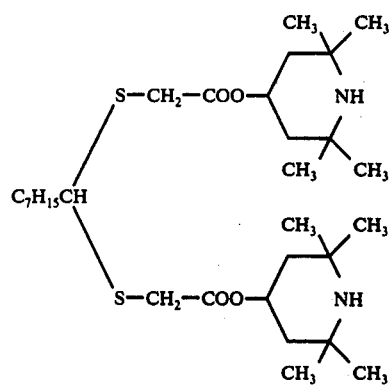
6.
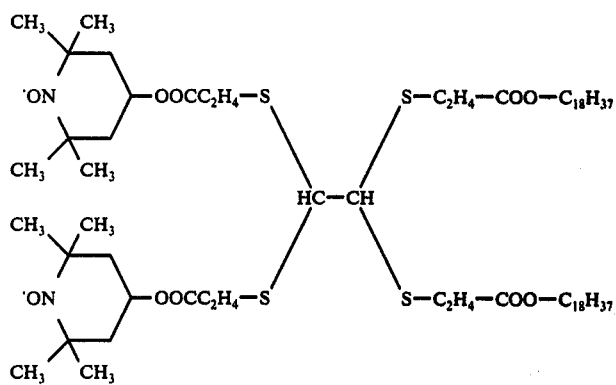
7.
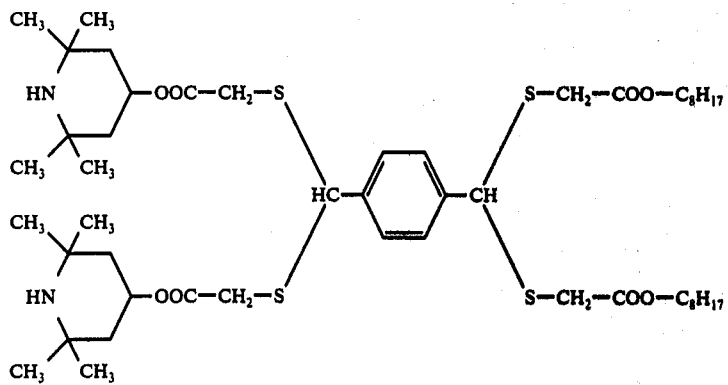

-continued
8.
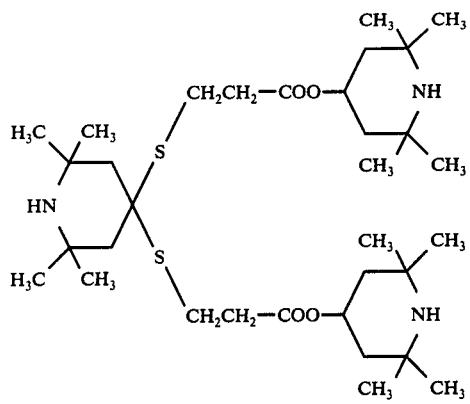
9.
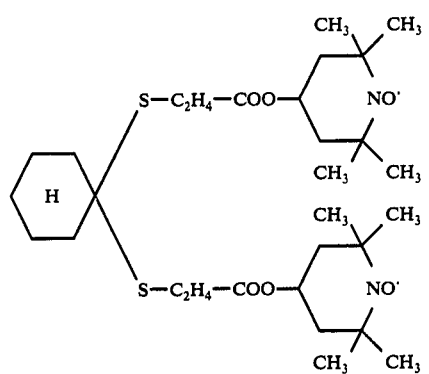
10.
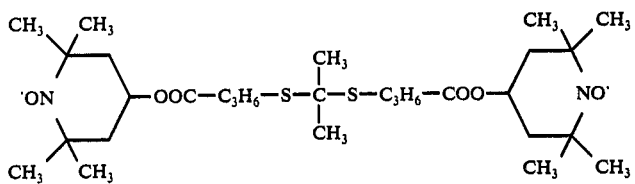
11.
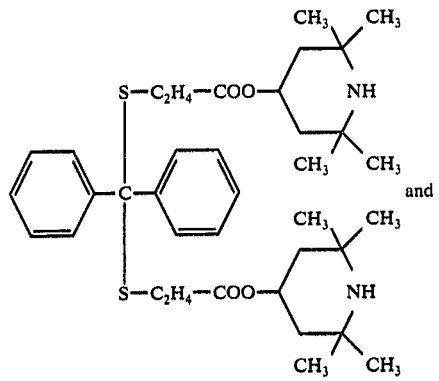
and
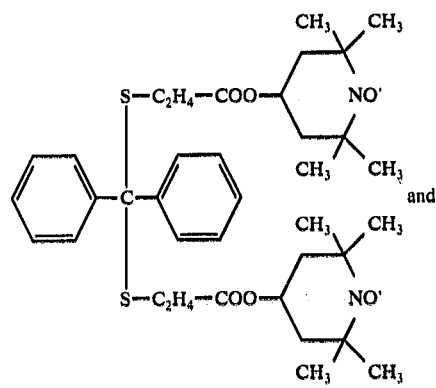

-continued
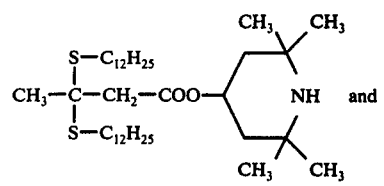 12.
and
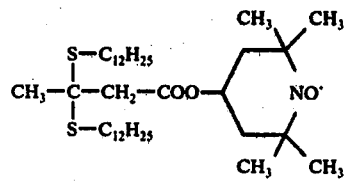
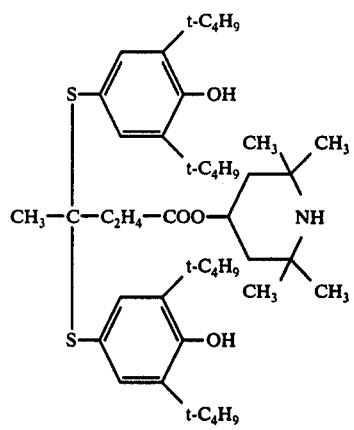 13.
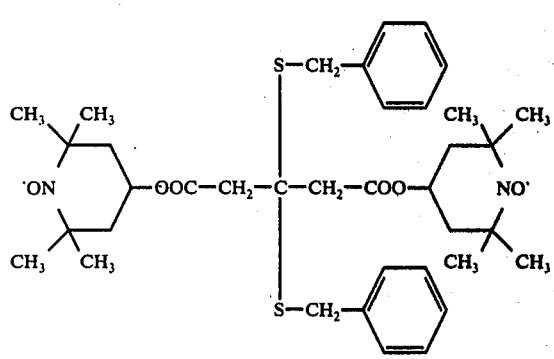 14.
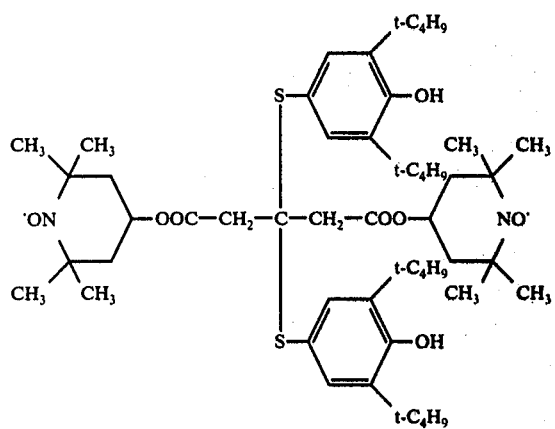 15.

-continued
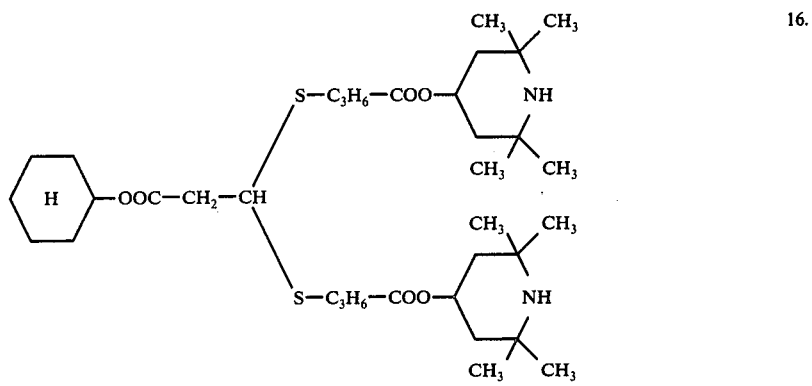
16.
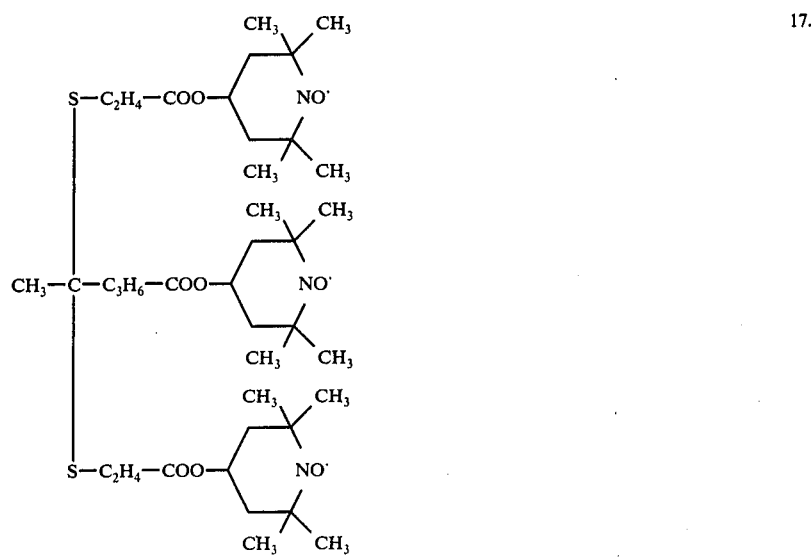
17.
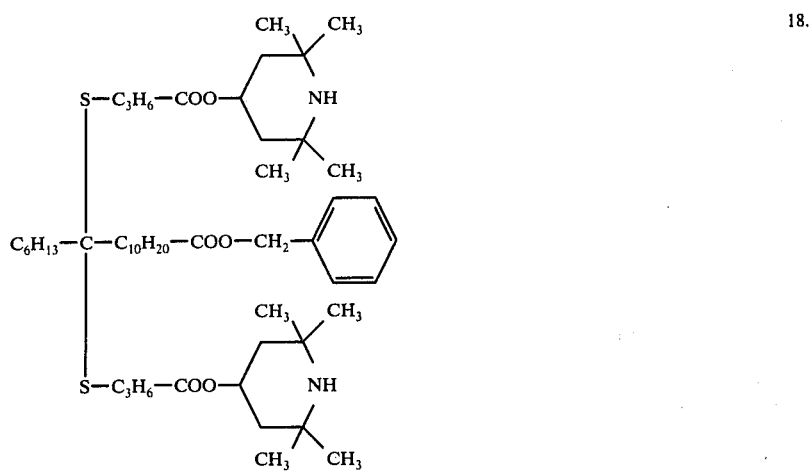
18.

-continued
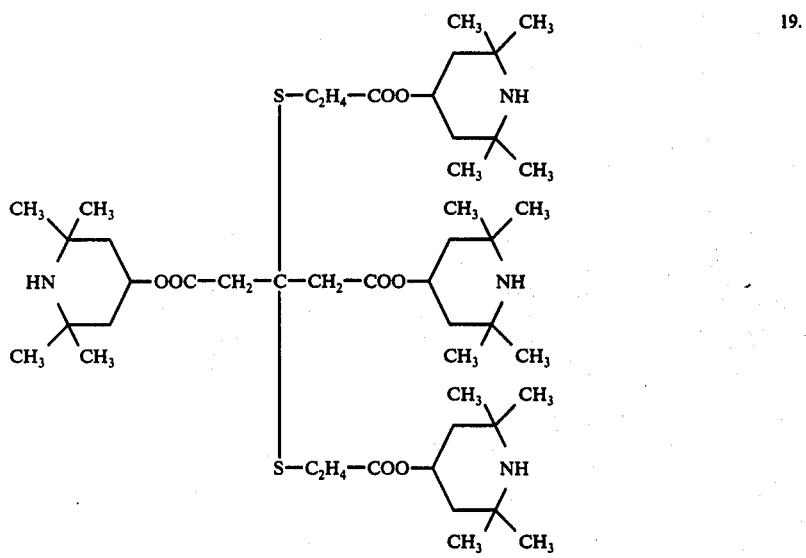
19.
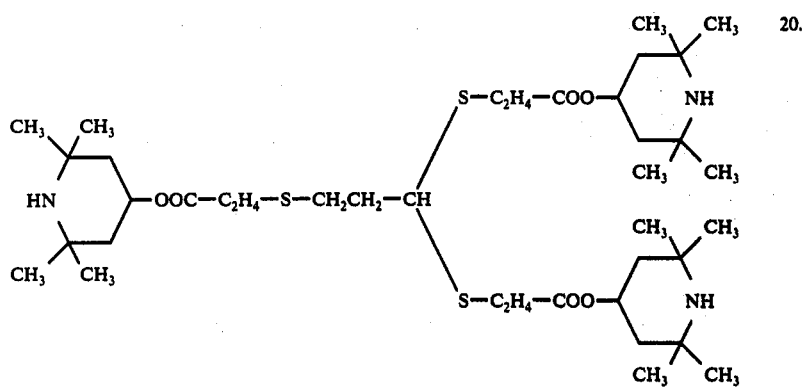
20.
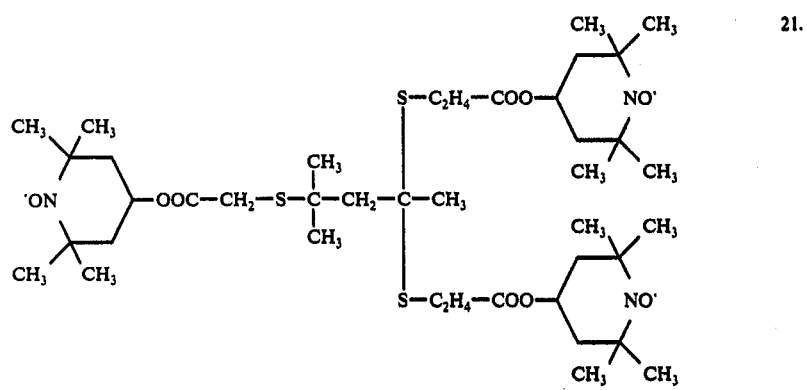
21.
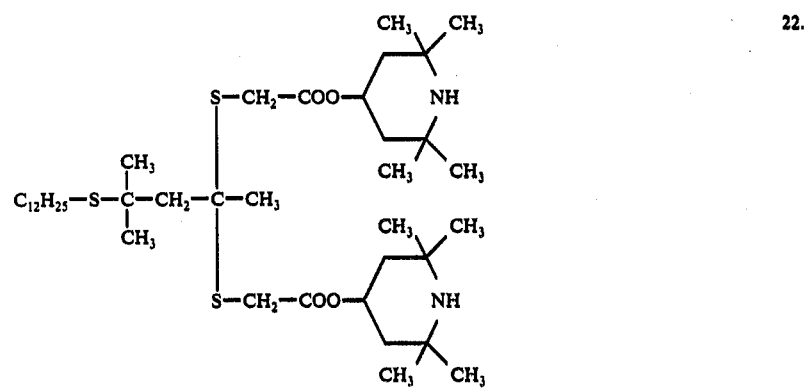
22.

-continued
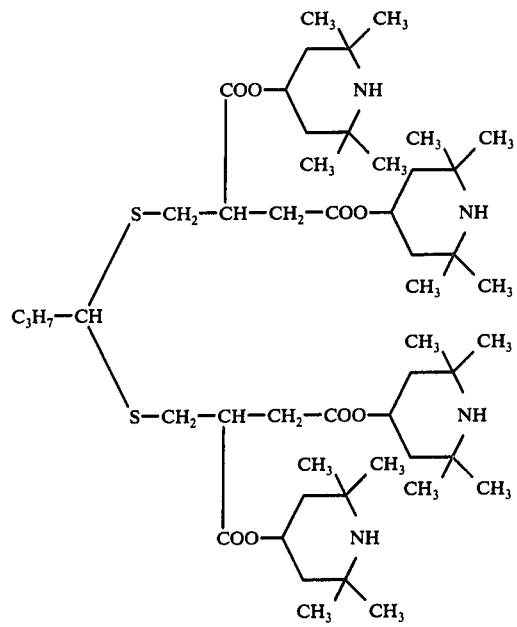 23.
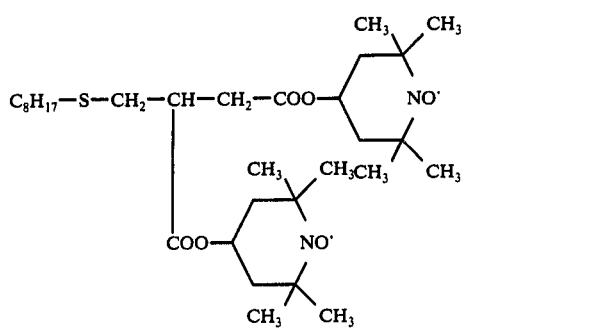 24.
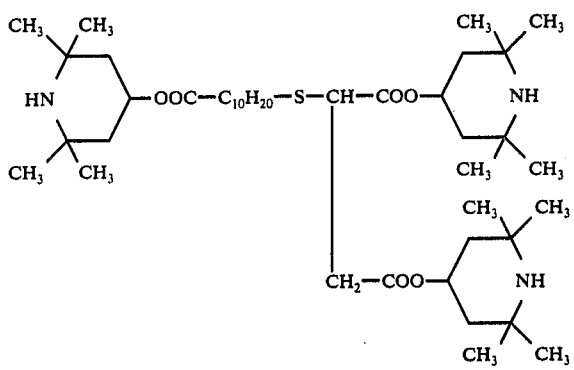 25.
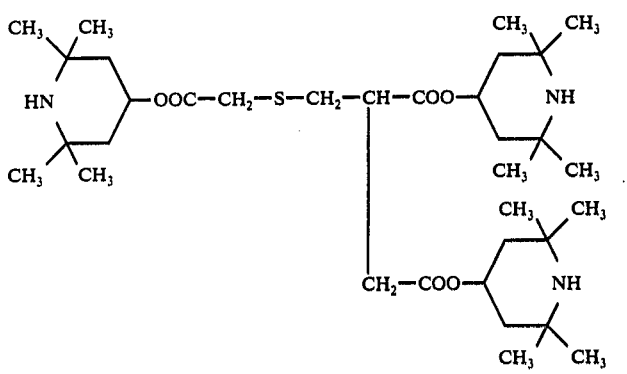 26.

-continued
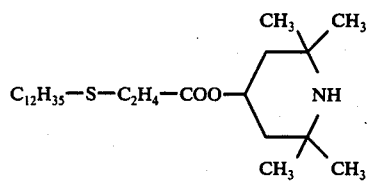 27.
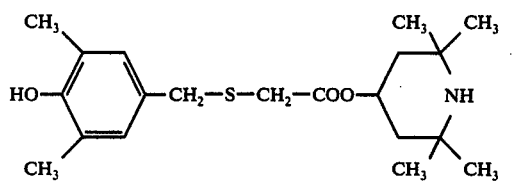 28.
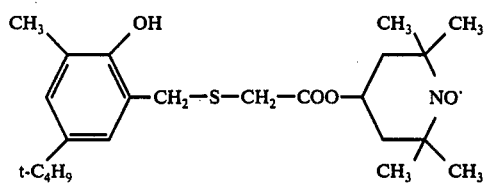 29.
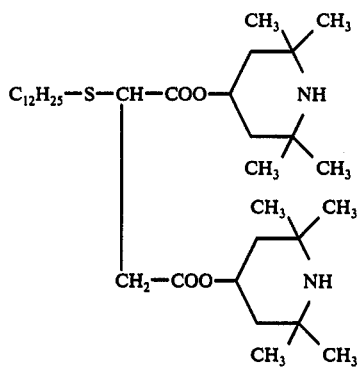 30.
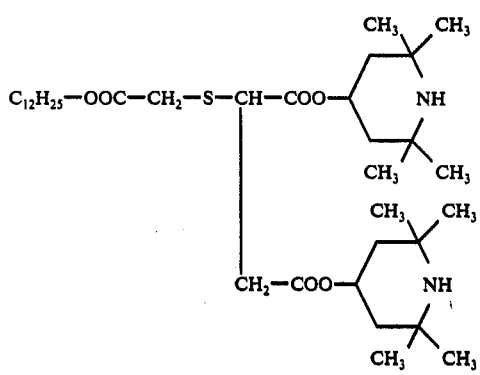 31.
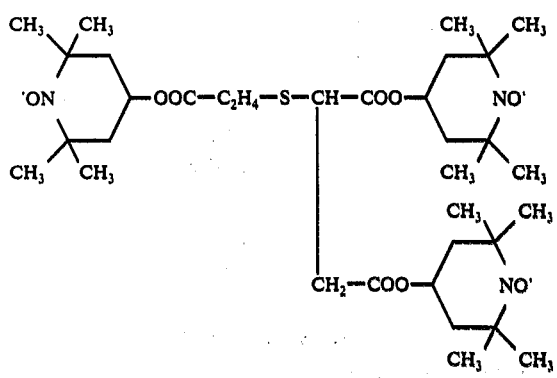 32.

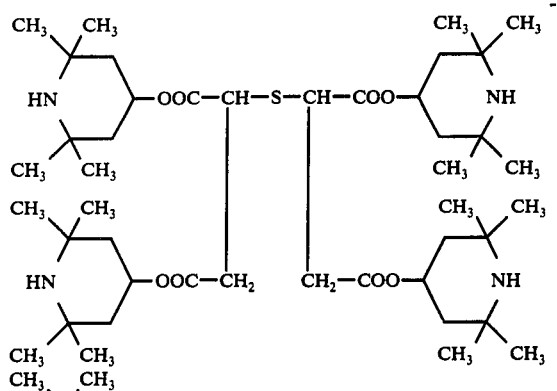

33.

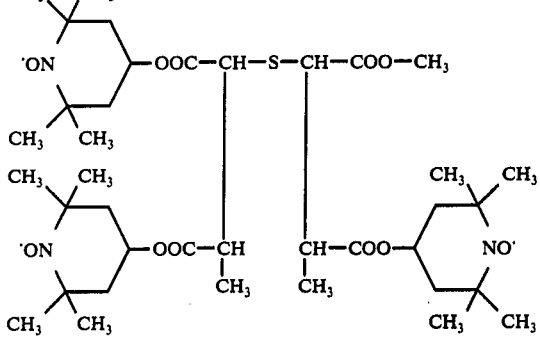

34.

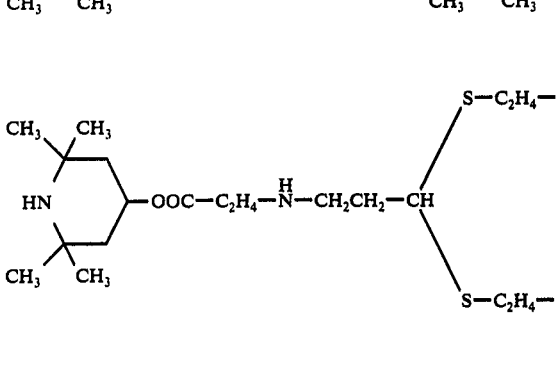

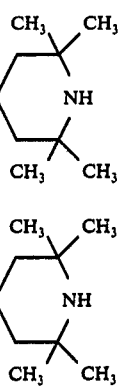

35.

The following Example illustrates the preparation of the amino carboxylate 2,2,6,6-tetramethyl-4-piperidyl compounds:

EXAMPLE III

A mixture was prepared of 23.3 g of trimethyl nitrilotriacetate, 61 g of 2,2,6,6-tetramethyl-piperidine-4-ol, 200 ml of xylene and 2 ml of a 12.5% methanol solution of sodium methoxide. The mixture was heated at 160° C for 6 hours. The solvent was then distilled off, and the resulting residue was then dissolved in n-hexane, and cooled under refrigeration until white crystals were obtained. The white crystals were identified as tris-(2,2,6,6-tetramethylpiperidine-4-yl)nitrilotriacetate, melting point 124° to 126° C. All peaks in the compound's infra-red spectrum are consistent with the following structure:

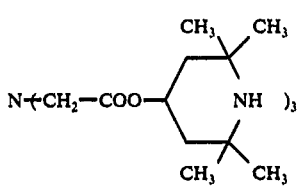

The powder was oxidized with peracetic acid, yielding a yellow powder.

The molecular weight found for this compound was 655, corresponding to a calculated molecular weight of 654 for the compound:

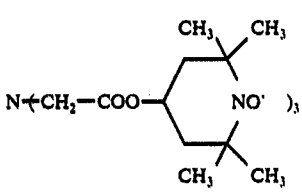

Using the above procedure, the following compounds were prepared:

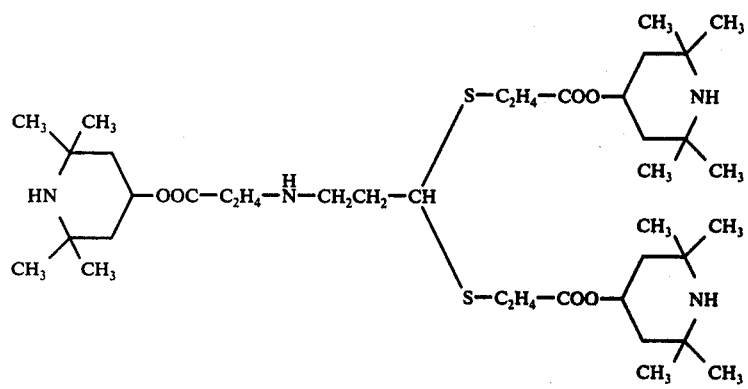
36.
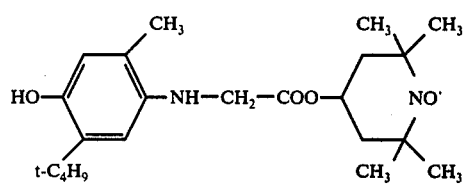
37.
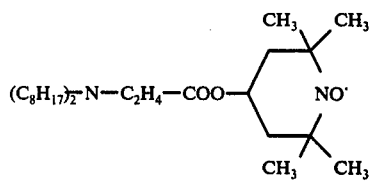
38.
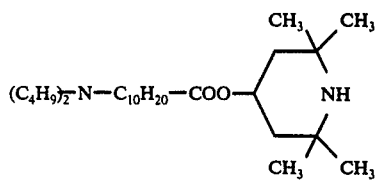
39.
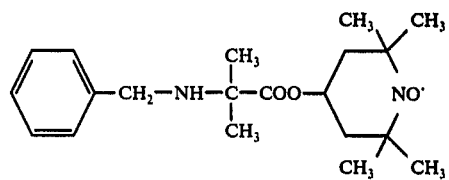
40.
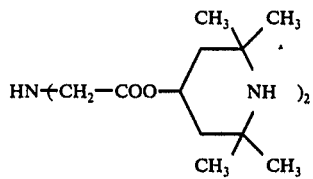
41.
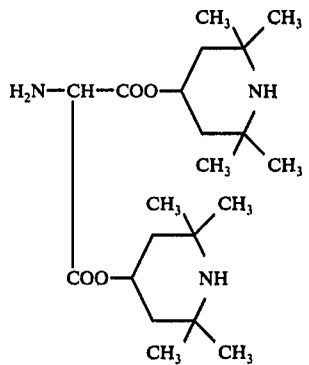
42.

-continued
43.
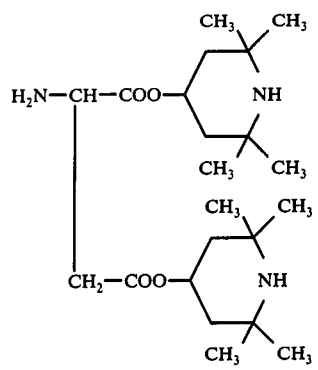
44.
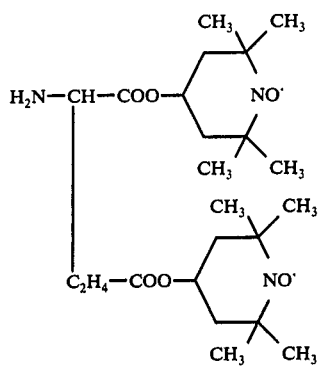
45.
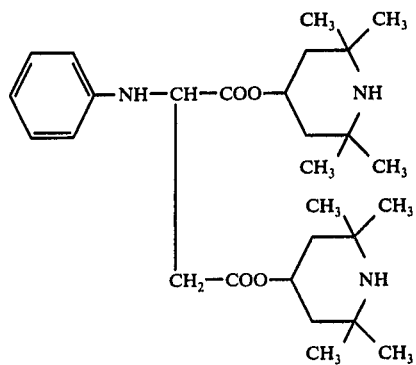
46.
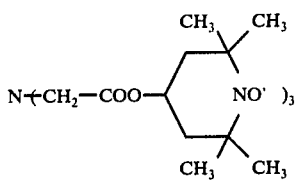
47.
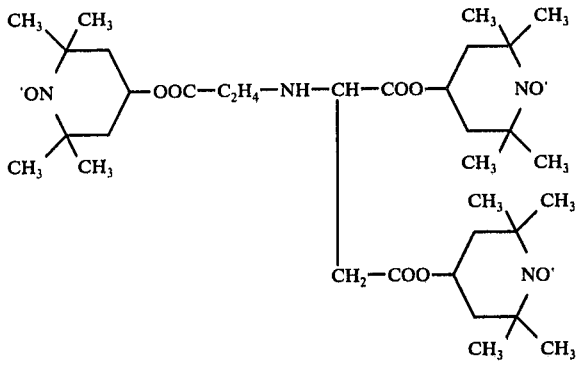

-continued
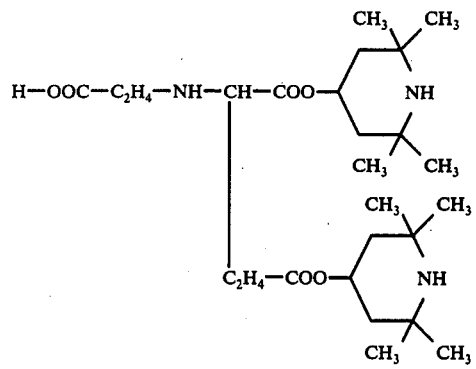
48.
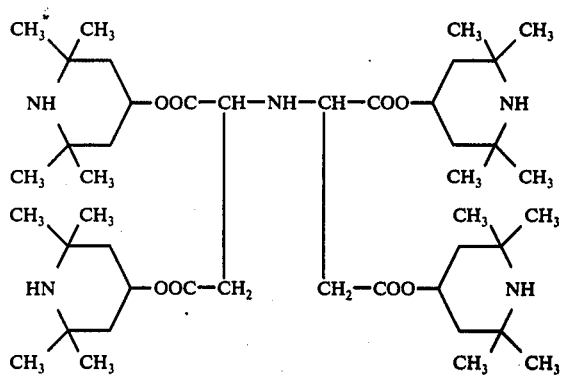
49.
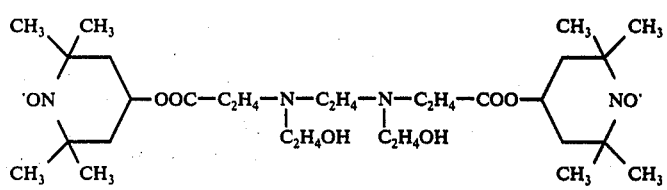
50.
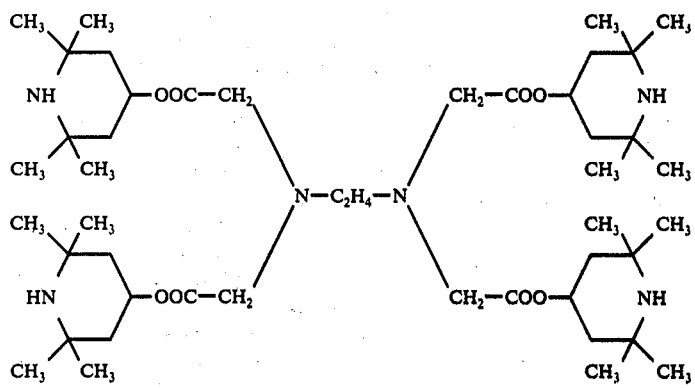
51.
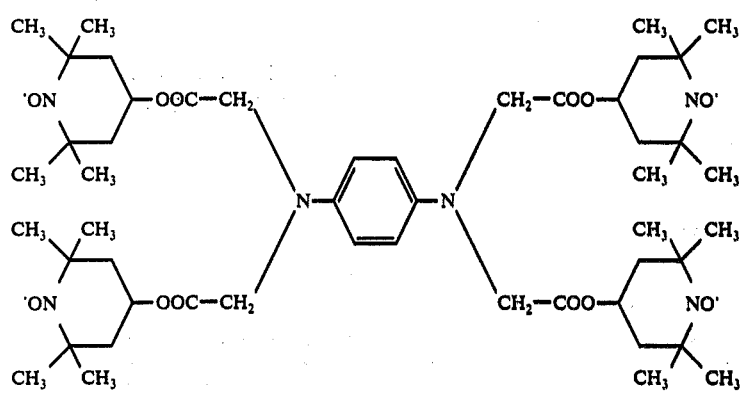
52.

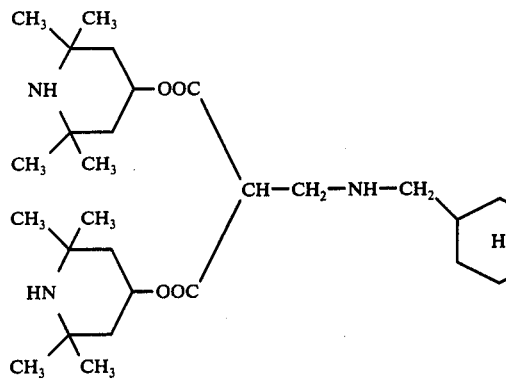
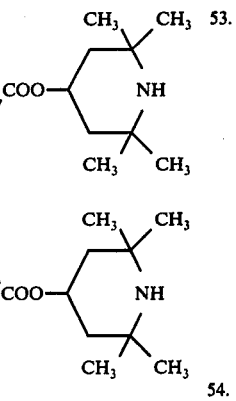
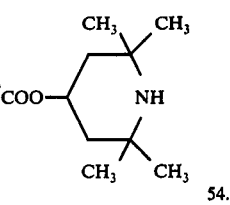
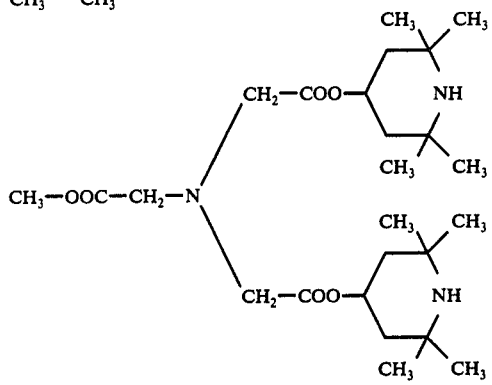

The 2,2,6,6-tetramethyl-4-piperidyl thiocarboxylic acid esters and amino carboxylic acid esters of the invention are effective stabilizers to enhance the resistance to deterioration due to heat and/or light of synthetic polymeric materials which are susceptible to such degradation, including polyolefins such as low density polyethylene, high density polyethylene, polypropylene, polybutylene, polyisobutylene, polypentylene, and polyisopentylene, polystyrene; polydienes, such as polybutadiene and polyisoprene; and copolymers of olefins and dienes with other ethylenically and acetylenically unsaturated monomers, such as ethylene-propylene copolymers, ethylene-butene copolymers, ethylene-pentene copolymers, ethylene-vinyl acetate copolymers, styrene-butadiene copolymers, acrylonitrile-styrene-butadiene copolymers, synthetic rubbers of all types, such as polychloroprene; polyvinyl halides, including polyvinyl chloride homopolymer, polyvinylidene chloride; and copolymers of vinyl chloride and vinylidene chloride; vinyl chloride and vinyl acetate; vinylidene chloride and vinyl acetate; and other ethylenically unsaturated monomers; polyacetals such as polyoxymethylene and polyoxyethylene; polyesters such as polyethylene glycol-terephthalic acid ester polymers; polyamides such as polyepsiloncaprolactam; polyhexamethylene adipamide and polydecamethylene adipamide; polyurethanes; and epoxy resins.

The synthetic polymer can be in any physical form, including (for example) filaments, yarns, films, sheets, molded articles, latex, and foam.

The stabilizers of the invention can be employed as the sole stabilizer or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organic triphosphites; organotin compounds; hindered phenols; and epoxy compounds.

With polyolefin resins there can be employed fatty acid salts to polyvalent metals, organic phosphites, phenolic antioxidants, and the higher fatty acid esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylonitrile butadiene stryene terpolymers, antioxidants such as hindered phenols and bis-phenols, polyvalent metal salts of the higher fatty acids, and organic phosphites can be used.

In addition, other conventional additives for synthetic polymers, such as plasticizers, lubricants, emulsifiers, antistatic agents, flameproofing agents, pigments and fillers, can be employed.

The following Examples in the opinion of the inventors represent preferred embodiments of synthetic resin compositions in accordance with the invention:

EXAMPLES 1 to 6

A group of polyvinyl chloride resin compositions was prepared having the following formulation:

| Ingredient | Parts by Weight |
| --- | --- |
| Polyvinyl chloride | 100 |
| Dioctylphthalate | 50 |
| Ca stearate | 1.0 |
| Zn stearate | 0.1 |
| Stabilizer as shown in Table I | 0.1 |

This formulation was blended and sheeted off on a two roll mill to form sheets 1 mm thick. The light resistance of these sheets was then determined by placing strips 1 cm long in a Weather-O-Meter, and exposing them to ultraviolet light. The time in hours was then noted for the sheet to develop a noticeable discoloration and/or embrittlement, indicating deterioration due to oxidation in the presence of ultraviolet light.

This test was carried out for the stabilizers having the formulae indicated in Table I. The following results were obtained:

TABLE I

| Example No. | Stabilizer | Hours to Failure |
|---|---|---|
| Control | 2-hydroxy-4-octoxybenzophenone | 360 |
| 1 | [bis(2,2,6,6-tetramethyl-4-piperidinyl) ester of thiodiglycolic-thiomethylene diacid: HN-piperidine-OOC-CH₂-S-CH₂-S-CH₂-COO-piperidine-NH] | 820 |
| 2 | [4,4-bis(2-((2,2,6,6-tetramethyl-4-piperidinyloxy)carbonyl)ethylthio)-2,2,6,6-tetramethylpiperidine] | 910 |
| 3 | [tetrakis(2,2,6,6-tetramethyl-4-piperidinyl) ester with two S-C₂H₄-COO- branches on central C] | 870 |
| 4 | [tris(2,2,6,6-tetramethyl-4-piperidinyl) ester: HN-pip-OOC-CH₂-S-CH₂-CH(COO-pip-NH)-CH₂-COO-pip-NH] | 760 |

TABLE I-continued

| Example No. | Stabilizer | Hours to Failure |
|---|---|---|
| 5 | [structure: 2,6-dimethyl-4-hydroxyphenyl-CH₂-S-CH₂-COO-tetramethylpiperidine(NH)] | 830 |
| 6 | [structure: tetra-substituted product with four tetramethylpiperidine(NH) groups linked through OOC-CH-S-CH-COO and OOC-CH₂, CH₂-COO] | 880 |

It is apparent that each of the six stabilizers in accordance with the invention is far superior to the control, a conventional ultraviolet light stabilizer for polyvinyl chloride, 2-hydroxy-4-octoxy-benzophenone.

EXAMPLES 7 to 13

Polypropylene compositions were prepared, seven stabilizers of the invention, and two of the prior art, and having the following formulation:

| Ingredient | Parts by Weight |
|---|---|
| Polypropylene | 100 |
| Distearylthiodipropionate | 0.3 |
| Goodrite 3114 (1,3,5-tris-(3′,5′-di-t-butyl 4′-hydroxybenzyl) isocyanurate) | 0.1 |
| Stabilizer as shown in Table II | 0.3 |

The compositions were thoroughly blended in a Brabender Plastograph, and then compression-molded to form sheets 0.5 mm thick. Pieces 2.5 cm square were cut off from the sheets and exposed to ultraviolet light in a Weather-O-Meter. The time in hours required for the sheet to develop a noticeable discoloration and/or embrittlement was noted as the hours to failure. The results obtained are shown in Table II.

TABLE II

| Example No. | Stabilizer | Hours to Failure |
|---|---|---|
| Control | Tinuvin-P (2-(2′-hydroxy-5′-methylphenyl)benzotriazole) | 340 |
| 7 | [structure: 3,5-di-t-butyl-4-hydroxyphenyl-CH with two S-C₂H₄-COO-tetramethylpiperidine(NH) groups] | 780 |
| 8 | [structure: tetramethylpiperidine(NO·)-OOC-C₃H₆-S-C(CH₃)₂-S-C₃H₆-COO-tetramethylpiperidine(NO·)] | 720 |

TABLE II-continued
| Example No. | Stabilizer | Hours to Failure |
|---|---|---|
| 9 | 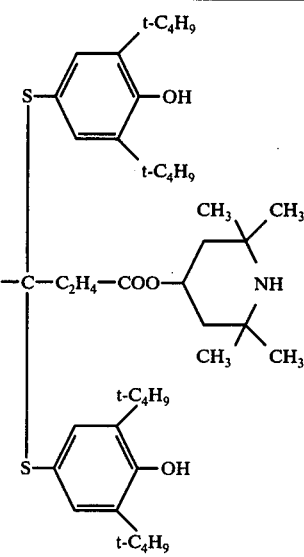 | 750 |
| 10 | 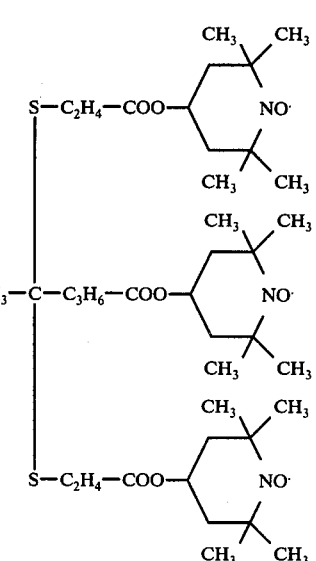 | 770 |
| 11 | 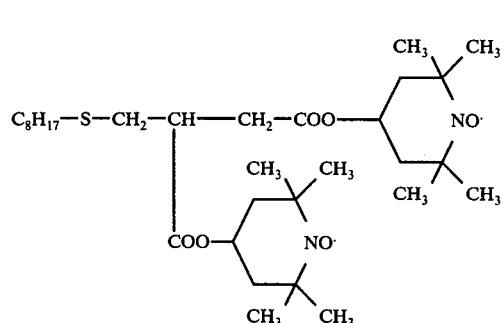 | 800 |
| 12 | 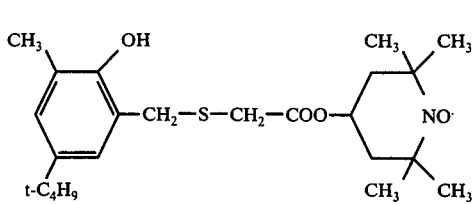 | 830 |

TABLE II-continued

| Example No. | Stabilizer | Hours to Failure |
|---|---|---|
| 13 | $C_{12}H_{25}-S-CH-COO-[2,2,6,6\text{-tetramethylpiperidinyl}]$ <br> $\quad\quad\quad\quad\quad\mid$ <br> $\quad\quad\quad\quad CH_2-COO-[2,2,6,6\text{-tetramethylpiperidinyl}]$ | 810 |

It is apparent from the above results that the compounds of the invention are superior stabilizers in enhancing the resistance of the polypropylene polymer composition to deterioration in the presence of ultraviolet light.

EXAMPLES 14 to 20

Ethylene-vinyl acetate copolymer compositions were prepared using stabilizers of the invention and one of the prior art, and having the following formulation:

| Ingredient | Parts by Weight |
|---|---|
| Ethylene-vinylacetate copolymer | 100 |
| Stabilizer as shown in Table III | 0.2 |

The stabilizer was blended with the polymer on a two-roll mill at 120° C, and sheets 1 mm thick were then compression molded at 120° C from the resulting blend. Pieces 2.5 cm square were cut off from the sheets and exposed to ultraviolet light in a Weather-O-Meter for 500 hours. At the start and at the conclusion of the test, the tensile strength of the sheet samples was determined. The results are given in Table III as % retention of the initially determined tensile strength:

TABLE III

| Example No. | Stabilizer | % Retention of Tensile Strength After 500 hours |
|---|---|---|
| Control | 2-hydroxy-4-methoxybenzophenone | 72 |
| 14 | $C_7H_{15}CH(S-CH_2-COO-[2,2,6,6\text{-tetramethylpiperidinyl}])_2$ | 78 |
| 15 | bis[2,2,6,6-tetramethylpiperidinyl-OOC-CH$_2$-S-CH-]-C$_6$H$_4$-CH(S-CH$_2$-COO-C$_8$H$_{17}$)$_2$ | 79 |

TABLE III-continued

| Example No. | Stabilizer | % Retention of Tensile Strength After 500 hours |
|---|---|---|
| 16 | [structure: CH$_3$–C(S–C$_{12}$H$_{25}$)$_2$–CH$_2$–COO–(2,2,6,6-tetramethylpiperidin-4-yl) NH (NO·)] | 84 |
| 17 | [structure: bis(2,2,6,6-tetramethyl-1-oxylpiperidin-4-yl) ester of di(benzylthio)malonate type: ·ON–piperidinyl–OOC–CH$_2$–C(S–CH$_2$–C$_6$H$_5$)$_2$–CH$_2$–COO–piperidinyl–NO·] | 83 |
| 18 | [structure: HN–piperidinyl–OOC–C$_2$H$_4$–S–CH$_2$CH$_2$–CH(S–C$_2$H$_4$–COO–piperidinyl–NH)$_2$] | 80 |
| 19 | C$_{12}$H$_{25}$–S–C$_2$H$_4$–COO–(2,2,6,6-tetramethylpiperidin-4-yl)NH | 78 |
| 20 | [structure: C$_{12}$H$_{25}$–OOC–CH$_2$–S–CH(COO–piperidinyl-NH)(CH$_2$–COO–piperidinyl-NH)] | 85 |

It is apparent from the results that the stabilizer compositions in accordance with the invention are superior to 2-hydroxy-4-methoxybenzophenone in enhancing the resistance of the ethylene-vinyl acetate copolymer to deterioration in the presence of ultraviolet light.

EXAMPLES 21 to 27

High density polyethylene compositions were prepared, using seven stabilizers of the invention and two of the prior art, and having the following formulation:

| Ingredient | Parts by Weight |
|---|---|
| High density polyethylene | 100 |

| Ingredient | Parts by Weight |
|---|---|
| Stabilizer as shown in Table IV | 0.1 |

The stabilizer was blended with the polymer on a two-roll mill and sheets 0.5 mm thick were prepared by compression molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure and the results are reported in Table IV:

TABLE IV

| Example No. | Stabilizer | Hours to Failure |
|---|---|---|
| Control A | 2-hydroxy-4-methoxybenzophenone | 540 |
| Control B | Tinuvin-P (2-(2'-hydroxy-5'-methylphenyl)benzotriazole) | 610 |
| 21 | [structure: phenyl-CH with two S—CH₂—COO—(2,2,6,6-tetramethylpiperidin-4-yl) groups] | 1030 |
| 22 | [structure: 2,2,6,6-tetramethyl-4-piperidinyl with two S—CH₂CH₂—COO—(2,2,6,6-tetramethylpiperidin-4-yl) groups] | 1100 |
| 23 | [structure: cyclohexyl-OOC—CH₂—CH with two S—C₃H₆—COO—(2,2,6,6-tetramethylpiperidin-4-yl) groups] | 980 |

TABLE IV-continued

| Example No. | Stabilizer | Hours to Failure |
|---|---|---|
| 24 | (chemical structure) | 950 |
| 25 | (chemical structure) | 1080 |
| 26 | (chemical structure) | 1120 |
| 27 | (chemical structure) | 1060 |

The stabilizers of the invention are clearly superior to the controls in enhancing resistance of the polyethylene to degradation under ultraviolet light.

EXAMPLES 28 to 34

Acrylonitrile-butadiene-styrene terpolymer resin compositions were prepared using seven stabilizers of the invention and one of the prior art, and having the following formulation:

| Ingredient | Parts by Weight |
|---|---|
| Acrylonitrile-butadiene-styrene terpolymer | 100 |

| Ingredient | Parts by Weight |
|---|---|
| Stabilizer as shown in Table V | 0.1 |

The stabilizer was blended with the resin on a two-roll mill, and sheets 3 mm thick were prepared by compression molding of the resulting blend. Pieces 2.5 cm square were cut off from the sheets, and subjected to ultraviolet light in a Weather-O-Meter for 800 hours. Tensile strength before and after the test exposure was determined, and the results reported as the percent of tensile strength retained, at the end of this time, in Table V.

TABLE V

| Example No. | Stabilizer | % Tensile Strength Retained |
|---|---|---|
| Control | 2,2'-dihydroxy-4-methoxybenzophenone | 70 |
| 28 | 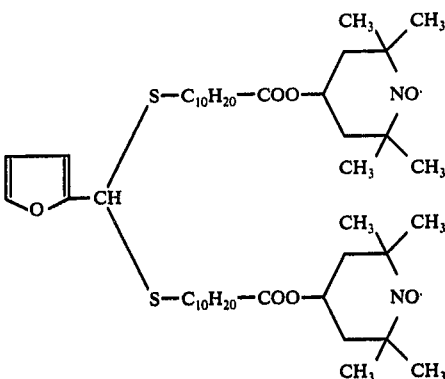 | 86 |
| 29 | 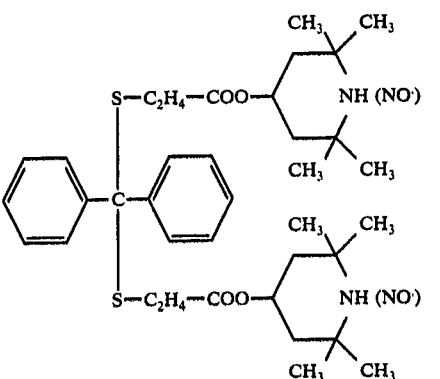 | 91 |
| 30 | 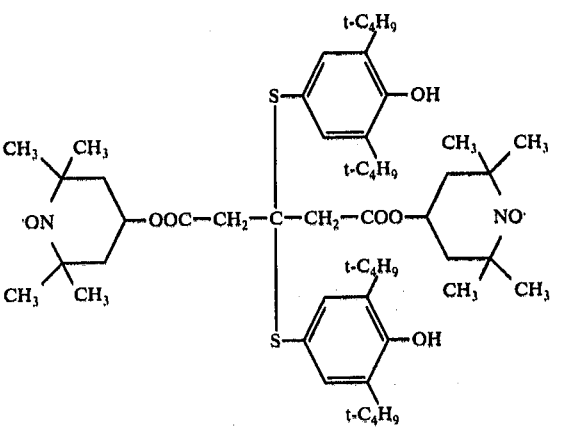 | 90 |

TABLE V-continued

| Example No. | Stabilizer | % Tensile Strength Retained |
|---|---|---|
| 31 | (2,2,6,6-tetramethylpiperidin-4-yl) HN—OOC—C$_{10}$H$_{20}$—S—CH—COO—(2,2,6,6-tetramethylpiperidin-4-yl)NH, with CH$_2$—COO—(2,2,6,6-tetramethylpiperidin-4-yl)NH branch | 92 |
| 32 | 3,5-dimethyl-4-hydroxybenzyl—S—CH$_2$—COO—(2,2,6,6-tetramethylpiperidin-4-yl)NH | 93 |
| 33 | C$_{12}$H$_{25}$—OOC—CH$_2$—S—CH—COO—(2,2,6,6-tetramethylpiperidin-4-yl)NH, with CH$_2$—COO—(2,2,6,6-tetramethylpiperidin-4-yl)NH branch | 92 |
| 34 | (2,2,6,6-tetramethyl-1-oxylpiperidin-4-yl)·ON—OOC—CH—S—CH—COO—CH$_3$, with ·ON—OOC—CH(CH$_3$) and CH(CH$_3$)—COO—NO· branches | 91 |

It is apparent from the data that the stabilizers of the invention are superior to the 2,2′-dihydroxy-4-methoxybenzophenone of the prior art.

EXAMPLES 35 to 41

Polyamide resin compositions were prepared using seven stabilizers of the invention and having the following formulation:

| Ingredient | Parts by Weight |
|---|---|
| Poly-epsilon-caprolactam | 100 |
| Stabilizer as shown in Table VI | 0.1 |

The stabilizer was blended with the finely powdered polyepsilon-caprolactam in a ball mill for fifteen minutes, and the resulting powder was then compression-molded at 250° C to form sheets 0.5 mm thick. Pieces 2.5 cm square were cut out from the sheets, and exposed to ultraviolet light in a Weather-O-Meter for 120 hours. At the conclusion of the test period, the color of the sheets was noted. The results are given in Table VI.

TABLE VI

| Example No. | Stabilizer | Color of Sheet |
|---|---|---|
| Control | None | Yellow |
| 35 | [structure: bis(2,2,6,6-tetramethylpiperidin-4-yl) ester with -OOC-CH₂-S-CH₂-S-CH₂-COO- linker] | |
| 36 | [structure: bis(1-oxyl-2,2,6,6-tetramethylpiperidin-4-yl) with -OOCC₂H₄-S- groups and HC-CH center bearing two S-C₂H₄-COO-C₁₈H₃₇ groups] | Pale Yellow |
| 37 | [structure: cyclohexane with H, bearing two S-C₂H₄-COO- groups linked to 1-oxyl-2,2,6,6-tetramethylpiperidin-4-yl] | None |
| 38 | [structure: C₆H₁₃-C(-C₁₀H₂₀-COO-CH₂-phenyl)(two S-C₃H₆-COO-2,2,6,6-tetramethylpiperidin-4-yl groups)] | None |

TABLE VI-continued

| Example No. | Stabilizer | Color of Sheet |
|---|---|---|
| 39 | (structure) | None |
| 40 | (structure) | None |
| 41 | (structure) | None |

It is apparent that the stabilizers of the invention are effective ultraviolet light stabilizers for polyamide resins.

EXAMPLES 42 to 45

A group of polyvinyl chloride resin compositions was prepared having the following formulation:

| Ingredient | Parts by Weight |
|---|---|
| Polyvinyl chloride | 100 |
| Dioctylphthalate | 50 |
| Ca stearate | 1.0 |
| Zn stearate | 0.1 |
| Stabilizer as shown in Table I | 0.1 |

This formulation was blended and sheeted off on a two-roll mill to form sheets 1 mm thick. The light resistance of these sheets was then determined by placing strips 1 cm long in a Weather-O-Meter, and exposing them to ultraviolet light. The time in hours was then noted for the sheet to develop a noticeable discoloration and/or embrittlement, indicating deterioration due to oxidation in the presence of ultraviolet light.

This test was carried out for the stabilizers having the formulae indicated in Table VII. The following results were obtained:

TABLE VII

| Example No. | Stabilizer | Hours to Failure |
|---|---|---|
| Control | 2-hydroxy-4-octoxybenzophenone | 360 |
| 42 | H₂N—CH—COO—[2,2,6,6-tetramethylpiperidin-4-yl (NH)] <br> \| <br> CH₂—COO—[2,2,6,6-tetramethylpiperidin-4-yl (NH)] | 650 |
| 43 | N—(CH₂—COO—[2,2,6,6-tetramethylpiperidin-4-yl (NO·)])₃ | 800 |
| 44 | H—OOC—C₂H₄—NH—CH—COO—[2,2,6,6-tetramethylpiperidin-4-yl (NH)] <br> \| <br> C₂H₄—COO—[2,2,6,6-tetramethylpiperidin-4-yl (NH)] | 780 |
| 45 | CH₃—OOC—CH₂—N(CH₂—COO—[2,2,6,6-tetramethylpiperidin-4-yl (NH)])₂ | 840 |

It is apparent that each of the stabilizers in accordance with the invention is far superior to the control, a conventional ultraviolet light stabilizer for polyvinyl chloride, 2-hydroxy-4-octoxybenzophenone.

EXAMPLES 46 to 49

Polypropylene compositions were prepared using stabilizers of the invention and of the prior art, having the following formulation:

| Ingredient | Parts by Weight |
|---|---|
| Polypropylene | 100 |
| Distearylthiodipropionate | 0.3 |
| Goodrite 3114 (1,3,5-tris-(3',5'-di-t-butyl 4'-hydroxybenzyl) isocyanurate) | 0.1 |

| Ingredient | Parts by Weight |
|---|---|
| Stabilizer as shown in Table VIII | 0.3 |

The compositions were thoroughly blended in a Brabender Plastograph, and then compression-molded to form sheets 0.5 mm thick. Pieces 2.5 cm square were cut off from the sheets and exposed to ultraviolet light in a Weather-O-Meter. The time in hours required for the sheet to develop a noticeable discoloration and/or embrittlement was noted as the hours to failure. The results obtained are shown in Table VIII.

EXAMPLES 50 to 54

Ethylene-vinyl acetate copolymer compositions were prepared using stabilizers of the invention and one of the prior art, and having the following formulation:

| Ingredient | Parts by Weight |
|---|---|
| Ethylene-vinylacetate copolymer | 100 |
| Stabilizer as shown in Table IX | 0.2 |

The stabilizer was blended with the polymer on a two-roll mill at 120° C, and sheets 1 mm thick were then

TABLE VIII

| Example No. | Stabilizer | Hours to Failure |
|---|---|---|
| Control | Tinuvin-P (2-(2'-hydroxy-5'-methylphenyl)benzotriazole) | 340 |
| 46 | 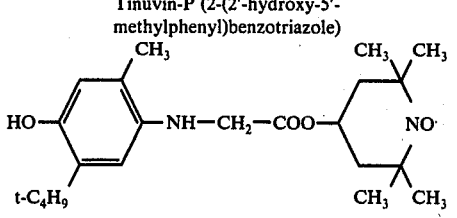 | 760 |
| 47 | 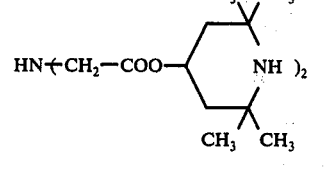 | 800 |
| 48 | 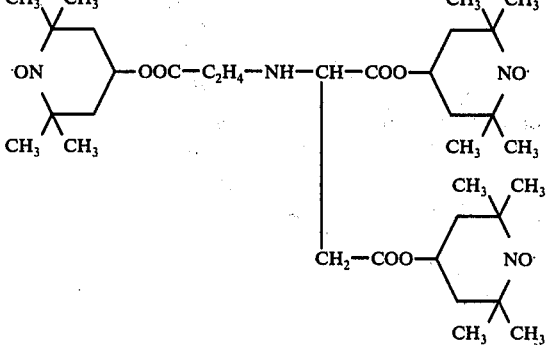 | 740 |
| 49 | 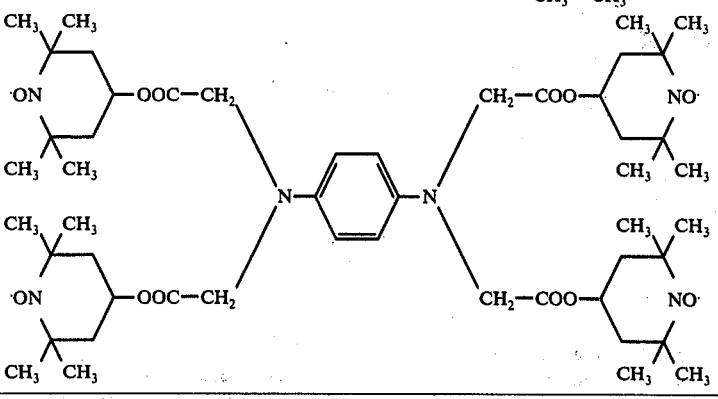 | 760 |

It is apparent from the above results that the compounds of the invention are superior stabilizers in enhancing the resistance of the polypropylene polymer composition to deterioration in the presence of ultraviolet light.

compression molded at 120° C from the resulting blend. Pieces 2.5 cm square were cut off from the sheets and exposed to ultraviolet light in a Weather-O-Meter for 500 hours. At the start and at the conclusion of the test, the tensile strength of the sheet samples was determined. The results are given in Table IX as % retention of the initially determined tensile strength:

TABLE IX

| Example No. | Stabilizer | % Retention of Tensile Strength After 500 hours |
|---|---|---|
| Control | 2-hydroxy-4-methoxybenzophenone | 72 |
| 50 | (C₈H₁₇)₂N—C₂H₄—COO—[2,2,6,6-tetramethyl-piperidinyl-N-O·] | 81 |
| 51 | C₆H₅—CH₂—NH—C(CH₃)₂—COO—[2,2,6,6-tetramethyl-piperidinyl-N-O·] | 80 |
| 52 | H₂N—CH(—COO—[2,2,6,6-tetramethyl-piperidinyl-N-O·])—C₂H₄—COO—[2,2,6,6-tetramethyl-piperidinyl-N-O·] | 77 |
| 53 | [2,2,6,6-tetramethyl-piperidinyl-N-O·]—OOC—C₂H₄—N(C₂H₄OH)—C₂H₄—N(C₂H₄OH)—C₂H₄—COO—[2,2,6,6-tetramethyl-piperidinyl-N-O·] | 81 |
| 54 | CH₃—OOC—CH₂—N(CH₂—COO—[2,2,6,6-tetramethyl-piperidinyl-NH])₂ | 82 |

It is apparent from the results that the stabilizer compositions in accordance with the invention are superior to 2-hydroxy-4-methoxybenzophenone in enhancing the resistance of the ethylene-vinyl acetate copolymer to deterioration in the presence of ultraviolet light.

EXAMPLES 55 to 57

High density polyethylene compositions were prepared using stabilizers of the invention and of the prior art, and having the following formulation:

| Ingredient | Parts by Weight |
|---|---|
| High density polyethylene | 100 |
| Stabilizer as shown in Table X | 0.1 |

The stabilizer was blended with the polymer on a two-roll mill and sheets 0.5 mm thick were prepared by compression molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure and the results are reported in Table X:

TABLE X

| Example No. | Stabilizer | Hours to Failure |
|---|---|---|
| Control A | 2-hydroxy-4-methoxybenzophenone | 540 |
| Control B | Tinuvin-P(2-(2'-hydroxy-5'-methylphenyl)benzotriazole) | 610 |
| 55 | [structure: phenyl-NH-CH(COO-tetramethylpiperidine-NH)-CH₂-COO-tetramethylpiperidine-NH] | 1050 |
| 56 | N(CH₂-COO-tetramethylpiperidine-NH)₃ | 1150 |
| 57 | [structure: N-C₂H₄-N bridged tetrakis(tetramethylpiperidinyl) ester] | 1090 |

The stabilizers of the invention are clearly superior to the controls in enhancing resistance of the polyethylene to degradation under ultraviolet light.

EXAMPLES 58 to 61

Acrylonitrile-butadiene-styrene terpolymer resin compositions were prepared using stabilizers of the invention and of the prior art, and having the following formulation:

| Ingredient | Parts by Weight |
|---|---|
| Acrylonitrile-butadiene-styrene terpolymer | 100 |
| Stabilizer as shown in Table XI | 0.1 |

The stabilizer was blended with the resin on a two-roll mill, and sheets 3 mm thick were prepared by compression molding of the resulting blend. Pieces 2.5 cm square were cut off from the sheets, and subjected to ultraviolet light in a Weather-O-Meter for 800 hours. Tensile strength before and after the test exposure was determined, and the results reported as the percent of tensile strength retained, at the end of this time, in Table XI.

TABLE XI

| Ex. No. | Stabilizer | % Tensile Strength Retained |
|---|---|---|
| Control | 2,2'-dihydroxy-4-methoxybenzophenone | 70 |

TABLE XI-continued
| Ex. No. | Stabilizer | % Tensile Strength Retained |
|---|---|---|
| 58 | 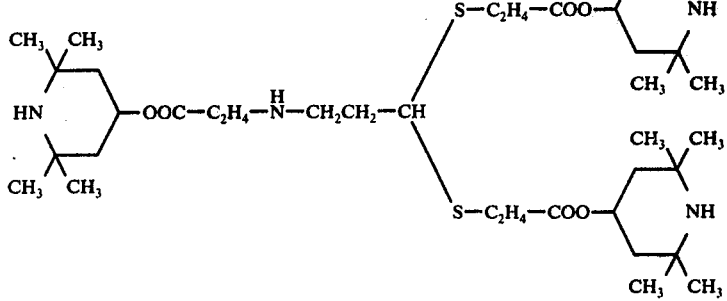 | 87 |
| 59 | 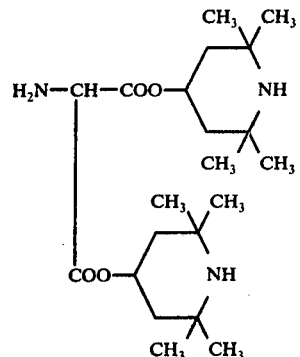 | 87 |
| 60 | 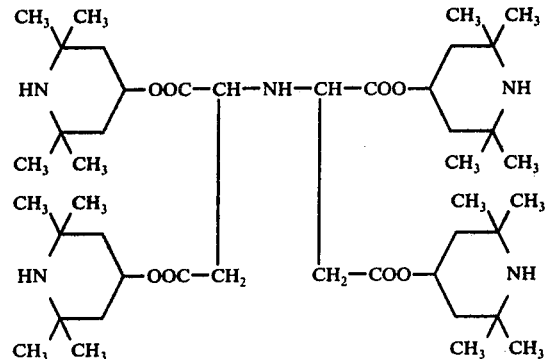 | 90 |
| 61 | 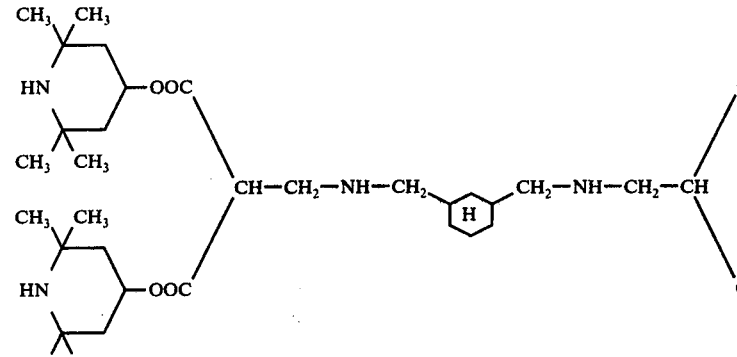 | 91 |
It is apparent from the data that the stabilizers of the invention are superior to the 2,2'-dihydroxy-4-methoxybenzophenone of the prior art.
EXAMPLES 62 and 63
Polyamide resin compositions were prepared using stabilizers of the invention and having the following formulation:

| Ingredient | Parts by Weight |
|---|---|
| Poly-epsilon-caprolactam | 100 |
| Stabilizer as shown in Table XII | 0.1 |

The stabilizer was blended with the finely powdered poly-epsiloncaprolactam in a ball mill for fifteen minutes, and the resulting powder was then compression molded at 250° C to form sheets 0.5 mm thick. Pieces 2.5 cm square were cut out from the sheets, and exposed to ultraviolet light in a Weather-O-Meter for 120 hours. At the conclusion of the test period, the color of the sheets was noted. The results are given in Table XII:

TABLE XII

| Example No. | Stabilizer | Color of Sheet |
|---|---|---|
| Control | None | Yellow |
| 62 | $(C_4H_9)_2-N-C_{10}H_{20}-COO-$[2,2,6,6-tetramethylpiperidin-4-yl] | Pale Yellow |
| 63 | [complex bis-piperidinyl structure with N-C2H4-N bridge] | None |

It is apparent that the stabilizers of the invention are effective ultraviolet light stabilizers for polyamide resins.

EXAMPLE 64

Polypropylene was compounded on the mill with the additives shown in the Table below, and dumbell specimens 0.5 mm thick prepared by injection molding from the milled sheets. Percent elongation was determined on molded samples either as made or after 305 hours Weather-O-Meter exposure.

| Ingredient | Parts by Weight |
|---|---|
| Polypropylene (Profax 6501 | 100 |
| n-Octadecyl-beta-(4-hydroxy-3,5-di-t-butylphenyl)propionate | 0.1 |
| Dilauryl thiodipropionate | 0.3 |
| Stabilizer listed in Table XIII | 0.1 |

The measured elongations before and after Weather-O-Meter exposure for 305 hours are tabulated in Table XIII:

TABLE XIII

| Ex. No. | Stabilizer | % Elongation Initial | % Elongation after 305 hours |
|---|---|---|---|
| Control | None | 344 | 4.4 |
| Control A | 2,2,6,6-tetramethyl-piperidine-4-yl benzoate | 193 | 3.3 |
| Control B | Bis (2,2,6,6-tetramethyl-piperidine-4-yl)sebacate | 308 | 3.9 |
| Control C | 2,2'-thiobis (p-t-octylphenol) n-butylamine nickel complex | 326 | 8.2 |
| 64 | Tetrakis (2,2,6,6-tetramethyl-piperidine-4-yl) thiodisuccinate (compound No. 34) | 297 | 18.3 |

The differences in initial elongation are not significant since elongation is very sensitive to imperfections in the samples.

The nickel compound stabilized control C is green, while the other are colorless. The elongation results show that the two piperidinyl esters are essentially without beneficial effect, the nickel complex has a modest beneficial effect, for which the green color must be accepted, and the thiodisuccinate ester of the invention is both more effective than the nickel complex and free of the objectionable color contribution.

EXAMPLE 65

Rectangular polypropylene samples 0.5 mm thick were irradicated with a mercury lamp with an output of radiation of 280 mm and higher wave lengths until they became brittle. The formulation was the same as in the preceding experiment except for the use of 0.3 part of stabilizer. The results were as follows:

TABLE XIV

| Ex. No. | Stabilizer | Hours to Embrittlement |
|---|---|---|
| Control | None | 72 |
| Control A | Bis(2,2,6,6-tetramethylpiperidine-4-yl)sebacate | 216 |
| 65 | tris(2,2,6,6-tetramethylpiperidine- | 425 |

TABLE XIV-continued

| Ex. No. | Stabilizer | Hours to Embrittlement |
|---|---|---|
| | 4-yl)nitrolotriacetate | 5 |

The superiority of Example 65 is clear.

EXAMPLE 66

Polypropylene was compounded with a conventional heat stabilizer combination and variable light stabilizer by mixing on the mill and compression molding 0.5 mm thick panels 15 cm square at 210° C for 6 minutes. Initial color was rated visually. 15 cm × 3 cm strips cut from the panels were exposed to light from a bank of fluorescent lamps 15 cm above the samples until failure by embrittlement.

The base formula was:

TABLE XV

| Ingredient | Parts by Weight |
|---|---|
| Polypropylene (Profax 6501) | 100 |
| Tris (3,5-di-t-butyl-4-hydroxybenzyl) isocyanurate | 0.15 |
| Distearyl thiodipropionate | 0.3 |
| Stabilizer listed in Table XVI | 0.5 |

Initial color, time to embrittlement in the Weather-O-Meter and heat stability, i.e. time to failure in a 150° air oven, are tabulated in Table XVI for each sample.

TABLE XVI

| Ex. | Light Stabilizer | Initial Color | Hours to failure at 150° C | Hours to Embrittlement |
|---|---|---|---|---|
| | None | Colorless | 3850 | 370 |
| Control 66 | 2-hydroxy-4-n-octyl-oxybenzophenone 0.5 | Slightly Yellow | 3140 | 1900 |
| | 2-hydroxy-4-n-octyl-oxybenzophenone 0.3 Tris (2,2,6,6-tetramethylpiperidine 4-yl) nitrilotriacetate 0.2 | Colorless | 4075 | 2175 |

These results show that with the conventional benzophenone type light stabilizer the beneficial effect on light stability is compensated by a sacrifice in early color and heat stability. With the inclusion of the amino acid ester of this invention in the combination, initial color and heat stability are at least as good as in the control and outstanding light stability is achieved.

Having regard to the foregoing disclosures, the following is claimed as the inventive and patentable embodiments thereof:

1. A 2,2,6,6-tetramethyl-4-piperidyl thiocarboxylates are provided having the general formula:

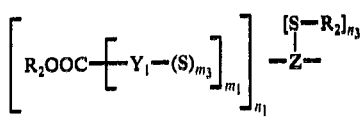

-continued

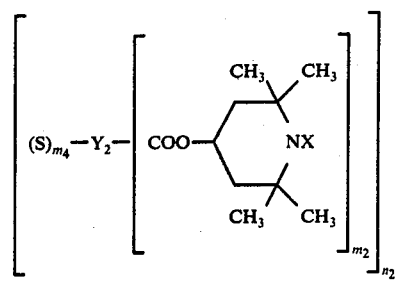

wherein:
$m_1$, $m_3$, and $m_4$ are numbers from 0 to 1;
$m_2$ is a number from 1 to 2;
$n_1$ is a number from 0 to 2;
$n_2$ is a number from 0 to 3;
$n_3$ is a number from 0 to 2;
$R_1$ is selected from the group consisting of alkyl, aralkyl, cycloalkyl and 2,2,6,6-tetramethyl-4-piperidyl;
$R_2$ is selected from the group consisting of alkyl, cycloalkyl, alkaryl, aralkyl, and hydroxy-substituted such radicals;
$R_1$ and $R_2$ have from one to about twenty carbon atoms;
X is hydrogen or O·;
$Y^1$ and $Y_2$ are bivalent linking radicals having from one to about twenty carbon atoms, and selected from the group consisting of alkylene and cycloalkylene; and amino-substituted such radicals;
Z is an organic radical having a valence from 2 to 4 and from one to about twenty carbon atoms, and selected from the group consisting of alkylene, alkylidene, aralkylene, aralkylidene, alkarylene, alkarylidene, heterocycloalkylene, heterocycloalkylidene, cycloalkylene and cycloalkylidene; amino-substituted such radicals and 2,2,6,6-tetramethyl-4-piperidylidene;
there being from one to four sulfur-containing such groups and at least one

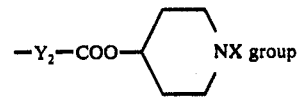

attached to the Z radical.

2. A compound according to claim 1 in which $n_1$ and $n_3$ are each zero, and $n_2$ is from 2 to 3.
3. A compound according to claim 1 in which $n_1$ and $n_2$ are each one or two, and $n_3$ is zero.
4. A compound according to claim 1 in which $n_2$ and $n_3$ are each one or two, and $n_1$ is zero.
5. A compound according to claim 1 in which X is hydrogen.
6. A compound according to claim 1 in which X is O·.
7. A compound according to claim 1 in which $Y_1$ and $Y_2$ are each alkylene.
8. A compound according to claim 1 in which $Y_1$ and $Y_2$ are each cycloalkylene.
9. A compound according to claim 1 in which Z is alkylene.
10. A compound according to claim 1 in which Z is alkylidene.

11. A compound according to claim 1 in which Z is phenylalkylidene.

12. A compound according to claim 1 in which there is one sulfur-containing such radical.

13. A compound according to claim 1 in which there are two sulfur-containing such radicals.

14. A compound according to claim 1 in which there are three sulfur-containing such radicals.

15. A compound according to claim 1 in which $n_1$ and $n_2$ are each one or two, $n_3$ is zero, $Y_1$ and $Y_2$ are each alkylene, Z is alkylene, and $m_4$ is one.

16. A compound according to claim 1 in which $n_1$ and $n_3$ are each zero, $n_2$ is one to three, Z is alkylene and $Y_2$ is alkylene, and $m_4$ is one.

17. A compound according to claim 1 having the formula:

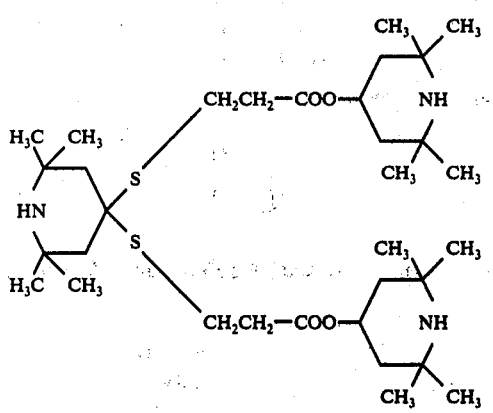

18. A compound according to claim 1 having the formula:

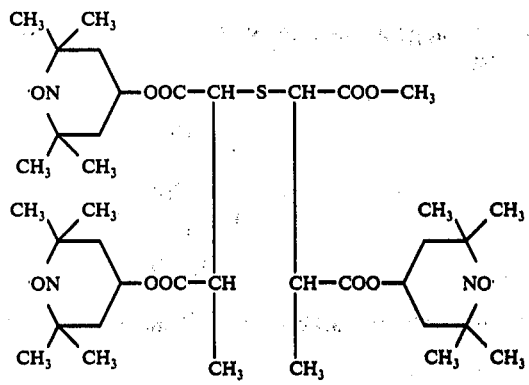

19. A polyvinyl chloride resin composition having improved resistance to deterioration when heated at 350° F, comprising a polyvinyl chloride resin formed at least in part of the recurring group

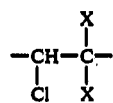

and having a chlorine content in excess of 40 percent, where X is either hydrogen or chlorine; and an amount to improve resistance to deterioration of the resin of a compound in accordance with claim 1.

20. A polyvinyl chloride resin composition in accordance with claim 19, in which the polyvinyl chloride resin is polyvinyl chloride homopolymer.

21. A polyvinyl chloride resin composition in accordance with claim 19, in which the polyvinyl chloride resin is a copolymer of vinyl chloride and vinyl acetate.

22. An olefin polymer composition having improved resistance to deterioration comprising an olefin polymer selected from the group consisting of polymers of alpha-olefins having from two to six carbon atoms and polystyrene, and an amount to improve resistance to deterioration of the resin of a compound in accordance with claim 1.

23. An olefin polymer composition in accordance with claim 22 wherein the polyolefin is polypropylene.

24. An olefin polymer composition in accordance with claim 22 wherein the polyolefin is polyethylene.

25. An acrylonitrile-butadiene-styrene polymer having improved resistance to deterioration when heated at 300° F and above and an amount to improve resistance to deterioration of the resin of a compound in accordance with claim 1.

26. A synthetic rubbery diene polymer composition having improved resistance to deterioration comprising a rubbery diene polymer and an amount to improve resistance to deterioration of the resin of a compound in accordance with claim 1.

27. A polyamide resin composition having improved resistance to deterioration comprising a polyamide resin and an amount to improve resistance to deterioration of the resin of a compound in accordance with claim 1.

28. An ethylene-vinyl acetate copolymer composition having improved resistance to deterioration comprising an ethylene-vinyl acetate copolymer and an amount to improve resistance to deterioration of the resin of a compound in accordance with claim 1.

29. A 2,2,6,6-tetramethyl-4-piperidyl aminocarboxylate having the formula:

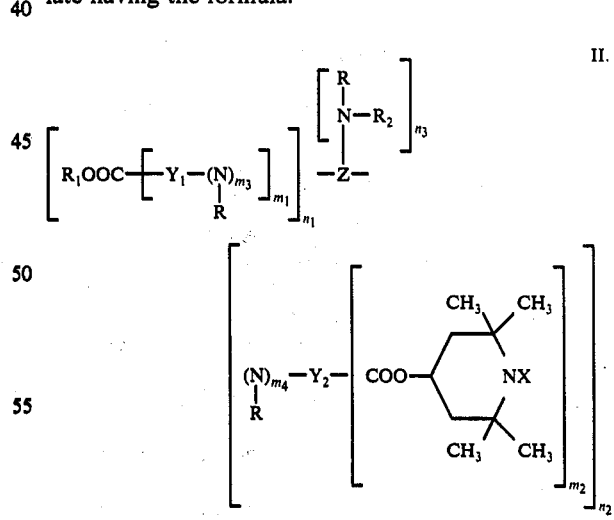

wherein:

$m_1$, $m_3$ and $m_4$ are numbers from 0 to 1;
$m_2$ is a number from 1 to 2;
$n_1$ is a number from 0 to 2;
$n_2$ is a number from 0 to 3;
$n_3$ is a number from 0 to 2;
R is selected from the group consisting of hydrogen, alkyl, hydroxyalkyl, aralkyl, cycloalkyl, alkaryl, 2,2,6,6-tetramethyl-4-piperidyl, $R_1OOCY_2$, phenyl, hydroxy phenyl and

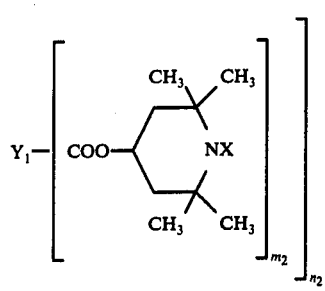

$R_1$ is selected from the group consisting of hydrogen, alkyl, aralkyl, cycloalkyl and 2,2,6,6-tetramethyl-4-piperidyl;

$R_2$ is selected from the group consisting of hydrogen, alkyl, cycloalkyl, aryl, alkaryl, aralkyl, and hydroxy-substituted such radicals;

R (when other than hydrogen), $R_1$ and $R_2$ have from one to about twenty carbon atoms;

X is hydrogen or O·;

$Y_1$ and $Y_2$ are bivalent linking radicals having from one to about twenty carbon atoms, and selected from the group consisting of alkylene and cycloalkylene; and Z is an organic radical having a valence from 2 to 4 and having from one to about twenty carbon atoms, and selected from the group consisting of alkylene, alkylidene, arylene, aralkylene, aralkylidene, alkarylene, alkarylidene, heterocycloalkylene, heterocycloalkylidene, cycloalkylene and cycloalkylidene;

there being from one to four nitrogen-containing such groups, and at least one

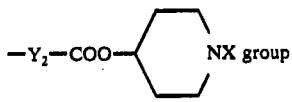

attached to the Z radical.

30. A compound according to claim 29 in which $n_1$ and $n_3$ are each zero, and $n_2$ is from 2 to 3.

31. A compound according to claim 29, in which $n_1$ and $n_2$ are each one or two, and $n_3$ is zero.

32. A compound according to claim 29 in which $n_2$ and $n_3$ are each one or two, and $n_1$ is zero.

33. A compound according to claim 29 in which X is hydrogen.

34. A compound according to claim 29 in which X is O·.

35. A compound according to claim 29 in which $Y_1$ and $Y_2$ are each alkylene.

36. A compound according to claim 1 in which Z is alkylene.

37. A compound according to claim 29 in which Z is alkylidene.

38. A compound according to claim 29 in which there is one nitrogen-containing such radical.

39. A compound according to claim 29 in which there are two nitrogen-containing such radicals.

40. A compound according to claim 29 in which there are three nitrogen-containing such radicals.

41. A compound according to claim 29 having the formula:

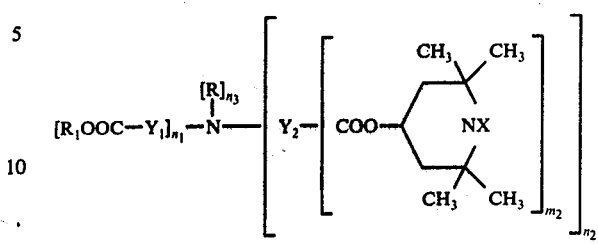

42. A compound according to claim 29 having the formula:

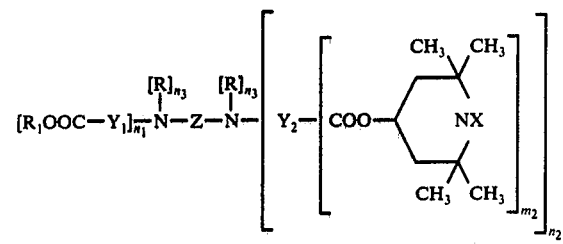

43. A compound according to claim 29 having the formula:

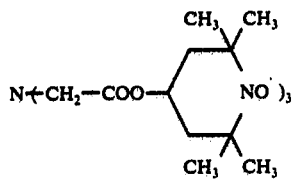

44. A compound according to claim 29 having the formula:

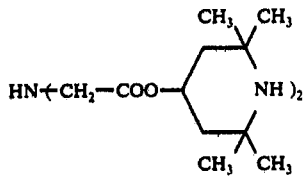

45. A compound according to claim 29 having the formula:

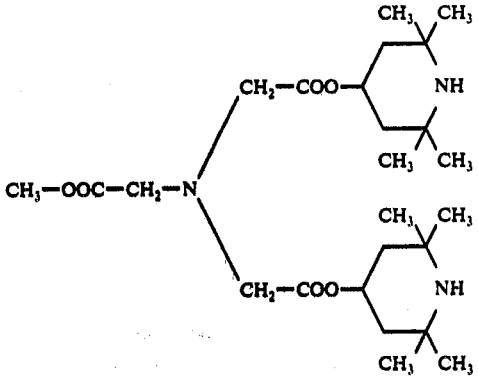

46. A compound according to claim 29 having the formula:

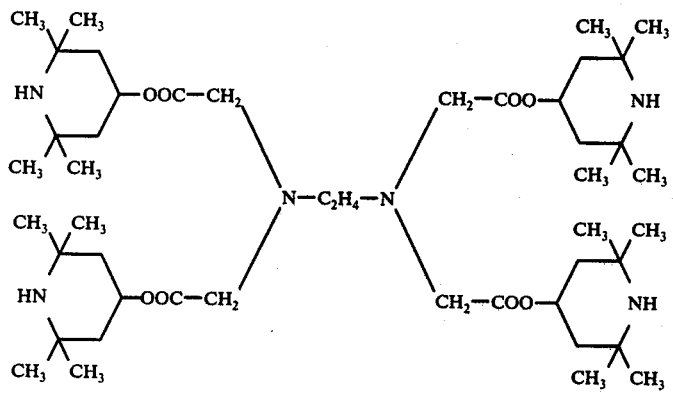

47. A polyvinyl chloride resin composition having improved resistance to deterioration when heated at 350° F, comprising a polyvinyl chloride resin formed at least in part of the recurring group

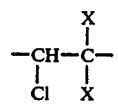

and having a chlorine content in excess of 40 percent, where X is either hydrogen or chlorine; and an amount to improve resistance to deterioration of the resin of a compound in accordance with claim 29.

48. A polyvinyl chloride resin composition in accordance with claim 47, in which the polyvinyl chloride resin is polyvinyl chloride homopolymer.

49. A polyvinyl chloride resin composition in accordance with claim 47, in which the polyvinyl chloride resin is a copolymer of vinyl chloride and vinyl acetate.

50. An olefin polymer composition having improved resistance to deterioration comprising an olefin polymer selected from the group consisting of polymers of alpha-olefins having from 2 to 6 carbon atoms and polystyrene, and an amount to improve resistance to deterioration of the resin of a compound in accordance with claim 29.

51. An olefin polymer composition in accordance with claim 50 wherein the polyolefin is polypropylene.

52. An olefin polymer composition in accordance with claim 50 wherein the polyolefin is polyethylene.

53. An acrylonitrile-butadiene-styrene polymer having improved resistance to deterioration when heated at 300° F and above and an amount to improve resistance to deterioration of the resin of a compound in accordance with claim 29.

54. A synthetic rubbery diene polymer composition having improved resistance to deterioration comprising a rubbery diene polymer and an amount to improve resistance to deterioration of the resin of a compound in accordance with claim 29.

55. A polyamide resin composition having improved resistance to deterioration comprising a polyamide resin and an amount to improve resistance to deterioration of the resin of a compound in accordance with claim 29.

56. An ethylene-vinyl acetate copolymer composition having improved resistance to deterioration comprising an ethylene-vinyl acetate copolymer and an amount to improve resistance to deterioration of the resin of a compound in accordance with claim 29.

57. A polyvinyl chloride resin composition having improved resistance to deterioration when heated at 350° F, comprising a polyvinyl chloride resin formed at least in part of the recurring group

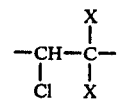

and having a chlorine content in excess of 40 percent, where X is either hydrogen or chlorine; and an amount to improve resistance to deterioration of the resin of a compound in accordance with claim 41.

58. A polyvinyl chloride resin composition having improved resistance to deterioration when heated at 350° F, comprising a polyvinyl chloride resin formed at least in part of the recurring group

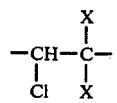

and having a chlorine content in excess of 40 percent, where X is either hydrogen or chlorine; and an amount to improve resistance to deterioration of the resin of a compound in accordance with claim 42.

* * * * *

UNITED STATES PATENT OFFICE
CERTIFICATE OF CORRECTION

Patent No. 4,102,858  Dated July 25, 1978

Inventor(s) Motonobu Minagawa et al

It is certified that error appears in the above-identified patent and that said Letters Patent are hereby corrected as shown below:

[57] Abstract, "⌈ " should be -- I. ⌈ -- .
⌊.                                      ⌊

[57] Abstract, line 32, "X is hydrogen or O;" should be -- X is hydrogen or O˙; --.

Column 7, line 62, "formla" should be --formula--.

Column 8, line 29, "or O ;" should be --or O˙; --.

Column 36, line 35, "to" should be --of--.

Column 36, line 44, "stryene" should be --styrene--.

Column 65, line 22, "NH)$_3$" should be --NO˙)$_3$ --.

Column 65, line 34, "N-C$_2$H$_4$N" should be -- N-C$_2$H$_4$-N --.

Column 69, line 60, insert -- ) -- after "(Profax 6501 ".

Column 70, line 58, "irradicated" should be -- irradiated --.

Column 71, line 5, "nitrolotriacetate" should be -- nitrilotriacetate --.

UNITED STATES PATENT OFFICE
CERTIFICATE OF CORRECTION

Patent No. 4,102,858   Dated July 25, 1978

Inventor(s) Motonobu Minagawa et al

It is certified that error appears in the above-identified patent and that said Letters Patent are hereby corrected as shown below:

Column 71, line 64, "

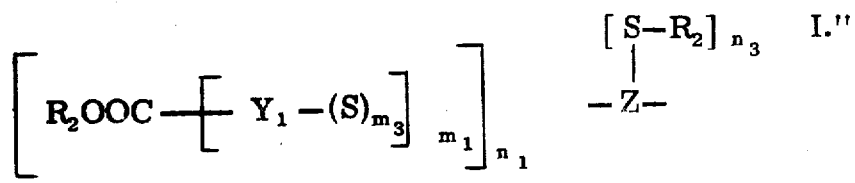

should be --

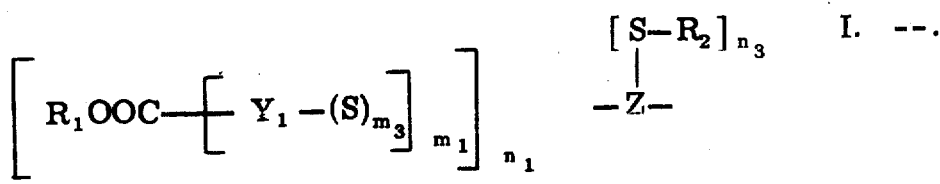

Column 72, line 28, " X is hydrogen or O ; " should be -- X is hydrogen or O˙ ; --.

Signed and Sealed this

Fourteenth Day of August 1979

[SEAL]

Attest:

LUTRELLE F. PARKER

*Attesting Officer*   *Acting Commissioner of Patents and Trademarks*